US008532727B2

(12) United States Patent
Ali et al.

(10) Patent No.: US 8,532,727 B2
(45) Date of Patent: *Sep. 10, 2013

(54) DUAL-MODE PULSE OXIMETER

(75) Inventors: Ammar Al Ali, Tustin, CA (US); Don Carothers, Mission Viejo, CA (US); David Dalke, Irvine, CA (US); Mohamed K. Diab, Mission Viejo, CA (US); Julian Goldman, Irvine, CA (US); Massi E. Kiani, Laguna Niguel, CA (US); Michael Lee, Aliso Viejo, CA (US); Jerome Novak, Aliso Viejo, CA (US); Robert Smith, Lake Forest, CA (US); Val E. Vaden, Hillsborough, CA (US)

(73) Assignee: Masimo Corporation, Irvine, CA (US)

( * ) Notice: Subject to any disclaimer, the term of this patent is extended or adjusted under 35 U.S.C. 154(b) by 641 days.

This patent is subject to a terminal disclaimer.

(21) Appl. No.: 11/894,722

(22) Filed: Aug. 20, 2007

(65) Prior Publication Data

US 2008/0039701 A1 Feb. 14, 2008

Related U.S. Application Data

(63) Continuation of application No. 10/911,391, filed on Aug. 3, 2004, which is a continuation of application No. 09/641,542, filed on Aug. 18, 2000, now Pat. No. 6,770,028, which is a continuation-in-part of application No. 09/491,175, filed on Jan. 25, 2000, now abandoned.

(60) Provisional application No. 60/117,097, filed on Jan. 25, 1999, provisional application No. 60/161,565, filed on Oct. 26, 1999.

(51) Int. Cl.
*A61B 5/1455* (2006.01)
*A61B 5/00* (2006.01)

(52) U.S. Cl.
USPC ............................................ 600/323; 600/300

(58) Field of Classification Search
USPC ........................................ 600/300, 310, 323
See application file for complete search history.

(56) References Cited

U.S. PATENT DOCUMENTS 4,331,962 A  5/1982  Neumann
4,704,007 A  11/1987  Landre et al.

(Continued)

FOREIGN PATENT DOCUMENTS

EP   0 553 372 A1   8/1993
EP   0 601 589      12/1993

(Continued)

OTHER PUBLICATIONS

A.L. Ronald et al., "Continuous Collection of Pulse Oximetry Data: New, Inexpensive, Portable computerized Method", British Journal of Anaesthesia 1992,69:105-107.

(Continued)

*Primary Examiner* — Eric Winakur
*Assistant Examiner* — Etsub Berhanu
(74) *Attorney, Agent, or Firm* — Knobbe Martens Olson & Bear LLP

(57) ABSTRACT

A portable stand alone patient monitor is dockable with a docking station attached to a patient bed. The portable monitor is configured to operate in a stand alone mode and a docked mode. The docking station can include a second local monitor.

26 Claims, 25 Drawing Sheets

(56) References Cited

U.S. PATENT DOCUMENTS

| | | | |
|---|---|---|---|
| 4,715,385 | A | 12/1987 | Cudahy et al. |
| 4,825,879 | A | 5/1989 | Tan et al. |
| 4,865,038 | A | 9/1989 | Rich et al. |
| 4,895,161 | A | 1/1990 | Cudahy et al. |
| 4,942,877 | A | 7/1990 | Sakai et al. |
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,111,817 | A | 5/1992 | Clark et al. |
| 5,159,936 | A | 11/1992 | Yelderman et al. |
| 5,163,438 | A | 11/1992 | Gordon et al. |
| 5,209,343 | A | 5/1993 | Romano et al. |
| 5,332,876 | A | 7/1994 | Romano et al. |
| 5,337,744 | A | 8/1994 | Branigan |
| 5,341,805 | A | 8/1994 | Stavridi et al. |
| 5,343,869 | A | 9/1994 | Pross et al. |
| D353,195 | S | 12/1994 | Savage et al. |
| D353,196 | S | 12/1994 | Savage et al. |
| 5,375,604 | A * | 12/1994 | Kelly et al. .................... 600/484 |
| 5,377,676 | A | 1/1995 | Vari et al. |
| 5,417,222 | A | 5/1995 | Dempsey et al. |
| D359,546 | S | 6/1995 | Savage et al. |
| 5,431,170 | A | 7/1995 | Mathews |
| 5,434,964 | A | 7/1995 | Moss et al. |
| D361,840 | S | 8/1995 | Savage et al. |
| D362,063 | S | 9/1995 | Savage et al. |
| 5,448,991 | A | 9/1995 | Polson et al. |
| D363,120 | S | 10/1995 | Savage et al. |
| 5,456,252 | A | 10/1995 | Vari et al. |
| 5,473,536 | A | 12/1995 | Wimmer |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,561,275 | A | 10/1996 | Savage et al. |
| 5,562,002 | A | 10/1996 | Lalin |
| 5,566,098 | A | 10/1996 | Lucente et al. |
| 5,579,001 | A | 11/1996 | Dempsey et al. |
| 5,590,649 | A | 1/1997 | Caro et al. |
| 5,602,924 | A | 2/1997 | Durand et al. |
| 5,627,531 | A | 5/1997 | Posso et al. |
| 5,632,272 | A | 5/1997 | Diab |
| 5,638,816 | A | 6/1997 | Kiani-Azarbayjany et al. |
| 5,638,818 | A | 6/1997 | Diab et al. |
| 5,640,627 | A | 6/1997 | Nakano et al. |
| 5,640,953 | A * | 6/1997 | Bishop et al. ................. 600/300 |
| 5,645,440 | A | 7/1997 | Tobler et al. |
| 5,661,632 | A | 8/1997 | Register |
| 5,661,658 | A | 8/1997 | Putt et al. |
| 5,685,299 | A | 11/1997 | Diab et al. |
| 5,685,314 | A * | 11/1997 | Geheb et al. ................. 600/513 |
| 5,687,717 | A | 11/1997 | Halpern et al. |
| D393,830 | S | 4/1998 | Tobler et al. |
| 5,743,262 | A | 4/1998 | Lepper, Jr. et al. |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,779,630 | A | 7/1998 | Fein et al. |
| 5,782,757 | A | 7/1998 | Diab et al. |
| 5,782,805 | A | 7/1998 | Meinzer et al. |
| 5,785,659 | A | 7/1998 | Caro et al. |
| 5,791,347 | A | 8/1998 | Flaherty et al. |
| 5,807,247 | A | 9/1998 | Merchant et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,918 | A | 1/1999 | Schradi et al. |
| 5,860,919 | A | 1/1999 | Kiani-Azarbayjany et al. |
| 5,868,710 | A | 2/1999 | Battiato et al. |
| 5,890,929 | A | 4/1999 | Mills et al. |
| 5,904,654 | A | 5/1999 | Wohltmann et al. |
| 5,910,797 | A | 6/1999 | Beuk |
| 5,910,882 | A | 6/1999 | Burnell |
| 5,913,823 | A * | 6/1999 | Hedberg et al. ................. 600/443 |
| 5,919,134 | A | 7/1999 | Diab |
| 5,931,791 | A | 8/1999 | Saltzstein et al. |
| 5,934,925 | A | 8/1999 | Tobler et al. |
| 5,940,182 | A | 8/1999 | Lepper, Jr. et al. |
| 5,944,659 | A * | 8/1999 | Flach et al. ..................... 600/300 |
| 5,947,907 | A * | 9/1999 | Duich ............................ 600/483 |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,134,504 | A | 10/2000 | Douglas et al. |
| 6,137,468 | A | 10/2000 | Martinez et al. |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab |
| 6,165,005 | A | 12/2000 | Mills et al. |
| 6,184,521 | B1 | 2/2001 | Coffin, IV et al. |
| 6,201,554 | B1 | 3/2001 | Lands |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,256,523 | B1 | 7/2001 | Diab et al. |
| 6,263,222 | B1 | 7/2001 | Diab |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,321,100 | B1 | 11/2001 | Parker |
| 6,322,502 | B1 | 11/2001 | Schoenberg et al. |
| 6,334,065 | B1 | 12/2001 | Al-Ali |
| 6,343,224 | B1 | 1/2002 | Parker |
| 6,349,228 | B1 | 2/2002 | Kiani et al. |
| 6,352,504 | B1 | 3/2002 | Ise et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,400,376 | B1 | 6/2002 | Singh et al. |
| 6,415,166 | B1 | 7/2002 | Van Hoy et al. |
| 6,430,525 | B1 | 8/2002 | Weber et al. |
| 6,441,828 | B1 | 8/2002 | Oba et al. |
| 6,453,173 | B1 | 9/2002 | Reber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab |
| 6,654,624 | B2 | 11/2003 | Diab et al. |

| | | |
|---|---|---|
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,704,007 B1 | 3/2004 | Clapper |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab |
| 6,760,607 B2 | 7/2004 | Al-Ali |
| 6,770,028 B1 | 8/2004 | Ali |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,254,953 B2 | 8/2007 | Callas et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |

| | | |
|---|---|---|
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,255,026 B1 | 8/2012 | Al-Ali |
| 8,255,028 B2 | 8/2012 | Al-Ali et al. |
| 8,260,577 B2 | 9/2012 | Weber et al. |
| 8,274,360 B2 | 9/2012 | Sampath et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,385,995 B2 | 2/2013 | Al-Ali et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 2002/0140675 A1 | 10/2002 | Ali et al. |
| 2002/0161291 A1 | 10/2002 | Kiani et al. |
| 2003/0197679 A1 | 10/2003 | Ali et al. |
| 2005/0065417 A1 | 3/2005 | Ali et al. |
| 2006/0258926 A1 | 11/2006 | Ali et al. |
| 2008/0030468 A1 | 2/2008 | Ali et al. |
| 2009/0076400 A1 | 3/2009 | Diab et al. |
| 2009/0099430 A1 | 4/2009 | Diab et al. |
| 2009/0182211 A1 | 7/2009 | Diab et al. |

FOREIGN PATENT DOCUMENTS

| | | |
|---|---|---|
| EP | 0601589 | 6/1994 |
| EP | 0 707 824 A2 | 4/1996 |
| EP | 0 707 825 A2 | 4/1996 |
| EP | 0 707 867 A2 | 4/1996 |
| EP | 0821911 | 2/1998 |
| EP | 1 460 516 A2 | 9/2004 |
| JP | 60-163633 | 8/1985 |
| JP | 62-8738 | 1/1987 |
| JP | 62-197032 | 8/1987 |
| JP | 2-55033 | 2/1990 |
| JP | 4-12736 | 1/1992 |
| JP | 4-176445 | 6/1992 |
| JP | 7-152553 | 6/1995 |
| WO | WO 87/00027 | 1/1987 |
| WO | WO 89/00061 | 1/1989 |
| WO | WO 94/24929 | 11/1994 |
| WO | WO 96-16591 | 6/1996 |
| WO | WO 97/08605 | 3/1997 |
| WO | WO 97/22293 | 6/1997 |
| WO | WO 98/11820 | 3/1998 |
| WO | WO 00/42911 | 7/2000 |
| WO | WO 0042911 | 7/2000 |
| WO | WO 00/64346 | 11/2000 |
| WO | WO 01/26232 A2 | 4/2001 |
| WO | WO 02/15781 A1 | 2/2002 |

OTHER PUBLICATIONS

Advertisement for MediSense Precision PCx Glucose Monitor, Sep. 1999.

British Journal of Anaesthesia, 1991, "The World's Most Advanced Pulse Oximetry System Just Became Even More Versatile," in 2 pages.

Chih-Lung Lin et al., "A Portable Monitor for Fetal Heart Rate and Uterine Contraction", IEEE Engineering in Medicine & Biology, Nov./Dec. 1997,80-84.

Comus International, 3 pages alleged to be downloaded and printed from the World Wide Web on Mar. 15, 2002.

Correll G. et al., "Evaluation of several blood glucose monitoring systems for whole blood glucose measurements at the point of care", 52nd Annual MCC Meeting, Jul. 23-27, 2000, Abstract 20.

David J. Farrar et al., "Portable Pneumatic Biventricular Driver for the Thoratec Ventricular Assist Device", ASAIO Journal 1997, 43: M631-M634.

Defendant/Counterclaim-Plaintiff Philips Electronics North America Corporation Answer to Masimo's Counterclaims, *Masimo Corporation v. Philips Electronics North America Corporation* and *Philips Medizin Systeme Böblingen GmbH*, (District of Delaware, Case No. 09-00080(JJF)) dated Aug. 3, 2009, pp. 1-23.

Defendants' Answer and Philips Electronics North America Corporation's Amended Counterclaims to Masimo's First Amended Complaint, *Masimo Corporation v. Philips Electronics North America Corporation* and *Philips Medizin Systeme Böblingen GmbH*, (District of Delaware, Case No. 09-00080(JJF)) dated Apr. 21, 2010.

European Patent Office Official Communication pursuant to Article 96(2) EPC, Application No. 01 962 370.1-2305, Mailing date: Jun. 28, 2007, in 4 pages.

European Search Report, App. No. 07021807.8-2310, dated Jul. 31, 2009 in 4 pages.

HP Component Monitoring System, Parameter Information, Edition 7—vol. 2, printed in Jul. 1994, in 252 pages.

HP Component Monitoring System, System Information, Edition 7—vol. 1, printed in Jul. 1994, in 252 pages.

HP VueLink and Baxter's Explorer and Vigilance Monitors, in 2 pages.

J.D.E. Van Suijlen et al., "New Trends in bedside blood glucose monitoring", Ned Tijdschr Klin Chem 2000, Apr. 6, 2000, vol. 25, No. 2.

James H. Nichols, "Management of Point-of-Care Testing", Blood Gas News, Dec. 9, 1999, vol. 8, No. 2.

Jing Bai et al., "Home Telemonitoring Framework Based on Integrated Functional Modules", IEEE 2000, Proceedings of the 22nd Annual EMBS Int'l Conference, Jul. 23-28, 2000,778-781.

M.1. Fikhman, "Problems in Cardiomonitoring System Design, Biomedical Engineering", vol. 29, No. 4, 199, 180-182.

M.Nakagawara and K. Yamakoshi, "A portable instrument for non-invasive monitoring of beat-by-beat cardiovascular haemodynamic parameters based on the volume-compensation and electrical-admittance method", Med. Biol. Eno. Cornput., 2000, vol. 38, 17-25.

*Mallinckrodt inc. v. Masimo Corp.*, 2004 U.S. Dist. LEXIS 28518 (C.D. Cal. Jul. 12, 2004).

Mallinckrodt Product Catalog, Jan. 18, 2000.

*Mallinckrodt, Inc. v. Masimo Corp.*, 147 Fed. Appx. 158, 2005 WL 2139867 (Fed. Cir. 2005).

Masimo's Answer to Philips' Amended Counterclaims, *Masimo Corporation v. Philips Electronics North America Corporation* and *Philips Medizin Systeme Böblingen GmbH*, (District of Delaware, Case No. 09-00080(JJF)) dated May 10, 2010.

Michael A.E. Schneider, et al., Use of a Relational Database for Patient- and Data-Management in the Electrophysiologic Catheter Laboratory', Computers in Cardiology 1994, 513-515.

N.D. Harris et al., "Can Changes in QT Interval be used to Predict the Onset of Hypoglycemia in Type 1 Diabetes?", Computers in Cardiology 2000; 27:375-278.
Nellcor PB N-200 Pulse Oximeter (NPN-200), in 4 pages.
P. Draycon, "Advanced technology in patient monitoring is expected to reduce costs", Min Invas Ther & Allied Technol1997: 6: 308-309.
Philips Electronics North America Corporation's Answer to Masimo's Amended Counterclaims, *Masimo Corporation v. Philips Electronics North America Corporation* and *Philips Medizin Systeme Böblingen GmbH*, (District of Delaware, Case No. 09-00080(JJF)) dated May 27, 2010.
Philips North America Corporation and Philips Medizin Systeme Böblingen GmbH's Seventh Supplemental Objections and Responses to Masimo Corporation's First Set of Interrogatories (Nos. 1-8), *Masimo Corporation v. Philips Electronics North America Corporation and Philips Medizin Systeme Böblingen GmbH*, (District of Delaware, Case No. 09-00080(JJF)) dated Jun. 30, 2010 (Redacted).
S. Weber, "Remote network (Ethernet) connectivity for glucose testing at the point-of-care", 51st Annual MCC Conference, Jul. 25-29, 1999, Abstract 111.
Service Manual, NELLCOR Interface/Display Module, Model N-50, 1992, in 21 pages.
Thoratec VADIVAD System Clinical Operation & Patient Management, 2004.
Toshiyo Tamura et al., "A system for monitoring temperature distribution in bed and its application to the assessment of body movement", Physiol. Meas. 14 (1993) 33-41.
U.S. Appl. No. 09/491,175, filed Jan. 25, 2000, now abandoned.
U.S. Appl. No. 10/153,263, filed May 21, 2002 in 48 pages.
U.S. Appl. No. 10/420,994, filed Apr. 22, 2003 in 48 pages.
U.S. Appl. No. 10/911,391, filed May 8, 2006 in 63 pages.
U.S. Appl. No. 11/431,151, filed May 8, 2006 in 49 pages.
U.S. Patent and Trademark Office Notice of Allowance, U.S. Appl. No. 09/516,110, Mailing date: Feb. 5, 2003, in 6 pages.
U.S. Patent and Trademark Office Notice of Allowance, U.S. Appl. No. 09/516,110, Mailing date: Sep. 11, 2002, in 9 pages.
U.S. Patent and Trademark Office Notice of Allowance, U.S. Appl. No. 09/641,542, Mailing date: Mar. 24, 2004, in 4 pages.
U.S. Patent and Trademark Office Office Action, U.S. Appl. No. 09/641,542, Mailing date: May 14, 2003, in 9 pages.
U.S. Patent and Trademark Office Office Action, U.S. Appl. No. 09/641,542, Mailing date: Oct. 10, 2002, in 9 pages.
U.S. Patent and Trademark Office Office Action, U.S. Appl. No. 09/641,542, Mailing date: Oct. 16, 2003, in 7 pages.
U.S. Patent and Trademark Office Office Action, U.S. Appl. No. 10/153,263, Mailing date: Apr. 30, 2007, in 12 pages.
U.S. Patent and Trademark Office Office Action, U.S. Appl. No. 10/153,263, Mailing date: Nov. 1, 2005, in 8 pages.
U.S. Patent and Trademark Office Office Action, U.S. Appl. No. 10/153,263, Mailing date: Sep. 22, 2004, in 11 pages.
U.S. Patent and Trademark Office Office Action, U.S. Appl. No. 10/153,263, Mailing date: Oct. 5, 2006, in 12 pages.
U.S. Patent and Trademark Office Office Action, U.S. Appl. No. 10/420,994, Mailing date: Feb. 24, 2006, in 6 pages.
U.S. Patent and Trademark Office Office Action, U.S. Appl. No. 10/420,994, Mailing date: Oct. 18, 2006, in 7 pages.
Copending U.S. Appl. No. 09/641,542, filed Aug. 18, 2000, and pending claims.
Copending U.S. Appl. No. 10/076,860, filed Feb. 12, 2002, and pending claims. (now patent No. 6,658,276).
Copending U.S. Appl. No. 10/153,263, filed May 21, 2002, and pending claims.
Copending U.S. Appl. No. 10/911,391, filed Aug. 3, 2004.
Copending U.S. Appl. No. 11/431,151, filed May 8, 2006.
Copending U.S. Appl. No. 12/039,704, filed Feb. 28, 2008.
*Masimo Corporation v. Philips Electronics North America Corporation* and *Philips Medizin Systeme Böblingen GmbH*, (District of Delaware, Case No. 09-000080(JJF)) Complaint for Patent Infringement dated Feb. 3, 2009.
*Masimo Corporation v. Philips Electronics North America Corporation* and *Philips Medizin Systeme Böblingen GmbH*, (District of Delaware, Case No. 09-00080(JJF)) First Amended Complaint for Patent Infringement dated May 12, 2009.
*Masimo Corporation v. Philips Electronics North America Corporation* and *Philips Medizin Systeme Böblingen GmbH*, (District of Delaware, Case No. 09-00080(JJF)) Defendants' Answer and Philips Electronics North America Corporation's Counterclaims to Masimo's First Amended Complaint dated Jun. 15, 2009.
*Masimo Corporation v. Philips Electronics North America Corporation* and *Philips Medizin Systeme Böblingen GmbH*, (District of Delaware, Case No. 09-00080(JJF)) Masimo's Answer to Philips' Counterclaims dated Jul. 9, 2009.
Extended European Search Report and European Search Opinion for App. No: 07021807.8-2310, dated Oct. 21, 2009 in 10 pages.
Extended European Search Report, App. No: 08012674.1-2310, dated Oct. 21, 2009 in 7 pages.
European Search Report, App. No. 09002646.9-2319, dated Nov. 17, 2010.
*Mallinckrodt, Inc. v. Masimo Corp.*, 254 F. Supp.2d 1140 (C.D. Cal. 2003).
Revised Joint Claim Construction Chart, *MASIMO Corporation v. Philips Electronics North America Corporation* and *Philips Medizin Systeme Böblingen GmbH*, (District of Delaware, Case No. 1:09-cv-00080 (LPS/MPT) dated Oct. 19, 2010.
Philips' Opening Markman Brief, *MASIMO Corporation v. Philips Electronics North America Corporation* and *Philips Medizin Systeme Böblingen GmbH*, (District of Delaware, Case No. 1:09-cv-00080 (LPS/MPT) dated Oct. 19, 2010.
MASIMO Corporation's Opening Claim Construction Brief, *MASIMO Corporation v. Philips Electronics North America Corporation* and *Philips Medizin Systeme Böblingen GmbH*, (District of Delaware, Case No. 1:09-cv-00080 (LPS/MPT) dated Oct. 19, 2010.
Declaration of Perry D. Oldham in Support of MASIMO Corporation's Opening Claim Construction Brief, *MASIMO Corporation v. Philips Electronics North America Corporation* and *Philips Medizin Systeme Böblingen GmbH*, (District of Delaware, Case No. 1:09-cv-00080 (LPS/MPT) dated Oct. 19, 2010.
Declaration of Robert T. Stone in Support of Philips' Responsive Markman Brief, *MASIMO Corporation v. Philips Electronics North America Corporation* and *Philips Medizin Systeme Böblingen GmbH*, (District of Delaware, Case No. 1:09-cv-00080 (LPS/MPT) dated Nov. 15, 2010.
MASIMO Corporation's Responsive Claim Construction Brief, *MASIMO Corporation v. Philips Electronics North America Corporation* and *Philips Medizin Systeme Böblingen GmbH*, (District of Delaware, Case No. 1:09-cv-00080 (LPS/MPT) dated Nov. 19, 2010 (Redacted).
Confidential Declaration of Michelle Armond in Support of MASIMO Corporation's Responsive Claim Construction Brief, *MASIMO Corporation v. Philips Electronics North America Corporation* and *Philips Medizin Systeme Böblingen GmbH*, (District of Delaware, Case No. 1:09-cv-00080 (LPS/MPT) dated Nov. 19, 2010 (Redacted).
Philips' Responsive Markman Brief, *MASIMO Corporation v. Philips Electronics North America Corporation* and *Philips Medizin Systeme Böblingen GmbH*, (District of Delaware, Case No. 1:09-cv00080 (LPS/MPT) dated Nov. 22, 2010.
Masimo's Technical Tutorial, *MASIMO Corporationv. Philips Electronics North America Corporation* and *Philips Medizin Systeme Böblingen GmbH*, (District of Delaware, Case No. 1:09-cv-00080 (LPS/MPT) dated Dec. 1, 2010.
Phlips' Claim Construction Hearing, Presentation Materials, *MASIMO Corporation v. Philips Electronics North America Corporation* and *Philips Medizin Systeme Böblingen GmbH*, (District of Delaware, Case No. 1:09-cv-00080 (LPS/MPT) dated Dec. 1, 2010.
Transcript of Markman Hearing, *MASIMO Corporation v. Philips Electronics North America Corporation* and *Philips Medizin Systeme Böblingen GmbH*, (District of Delaware, Case No. 1:09-cv00080 (LPS/MPT) dated Dec. 1, 2010.
Report and Recommendation re Claim Construction, *MASIMO Corporation v. Philips Electronics North America Corporation* and *Philips Medizin Systeme Böblingen GmbH*, (District of Delaware, Case No. 1:09-cv-00080 (LPS/MPT) dated Feb. 18, 2011.

\* cited by examiner

DUAL-MODE PULSE OXIMETER

PRIORITY CLAIM

This application is a continuation of U.S. patent application Ser. No. 10/911,391, entitled "Dual-Mode Pulse Oximeter," filed Aug. 3, 2004, which is a continuation of U.S. patent application Ser. No. 09/641,542, entitled "Dual-Mode Pulse Oximeter," filed Aug. 18, 2000, which is a continuation-in-part of U.S. patent application Ser. No. 09/491,175 entitled "Universal/Upgrading Pulse Oximeter," filed Jan. 25, 2000, now abandoned, which claims a priority benefit under 35 U.S.C. §119(e) from U.S. Provisional Patent Application No. 60/161,565, filed Oct. 26, 1999, entitled "Improved Universal/Upgrading Pulse Oximeter," and 60/117,097, filed Jan. 25, 1999, entitled "Universal/Upgrading Pulse Oximeter." The present applications also incorporate the foregoing utility disclosure herein by reference.

BACKGROUND

Oximetry is the measurement of the oxygen level status of blood. Early detection of low blood oxygen level is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximetry system generally consists of a sensor applied to a patient, a pulse oximeter, and a patient cable connecting the sensor and the pulse oximeter.

The pulse oximeter may be a standalone device or may be incorporated as a module or built-in portion of a multiparameter patient monitoring system, which also provides measurements such as blood pressure, respiratory rate and EKG. A pulse oximeter typically provides a numerical readout of the patient's oxygen saturation, a numerical readout of pulse rate, and an audible indicator or "beep" that occurs in response to each pulse. In addition, the pulse oximeter may display the patient's plethysmograph, which provides a visual display of the patient's pulse contour and pulse rate.

SUMMARY

FIG. 1 illustrates a prior art pulse oximeter 100 and associated sensor 110. Conventionally, a pulse oximetry sensor 110 has LED emitters 112, typically one at a red wavelength and one at an infrared wavelength, and a photodiode detector 114. The sensor 110 is typically attached to an adult patient's finger or an infant patient's foot. For a finger, the sensor 110 is configured so that the emitters 112 project light through the fingernail and through the blood vessels and capillaries underneath. The LED emitters 112 are activated by drive signals 122 from the pulse oximeter 100. The detector 114 is positioned at the fingertip opposite the fingernail so as to detect the LED emitted light as it emerges from the finger tissues. The photodiode generated signal 124 is relayed by a cable to the pulse oximeter 100.

The pulse oximeter 100 determines oxygen saturation ($SpO_2$) by computing the differential absorption by arterial blood of the two wavelengths emitted by the sensor 110. The pulse oximeter 100 contains a sensor interface 120, an $SpO_2$ processor 130, an instrument manager 140, a display 150, an audible indicator (tone generator) 160 and a keypad 170. The sensor interface 120 provides LED drive current 122 which alternately activates the sensor red and IR LED emitters 112. The sensor interface 120 also has input circuitry for amplification and filtering of the signal 124 generated by the photodiode detector 114, which corresponds to the red and infrared light energy attenuated from transmission through the patient tissue site. The $SpO_2$ processor 130 calculates a ratio of detected red and infrared intensities, and an arterial oxygen saturation value is empirically determined based on that ratio. The instrument manager 140 provides hardware and software interfaces for managing the display 150, audible indicator 160 and keypad 170. The display 150 shows the computed oxygen status, as described above. The audible indicator 160 provides the pulse beep as well as alarms indicating desaturation events. The keypad 170 provides a user interface for such things as alarm thresholds, alarm enablement, and display options.

Computation of $SpO_2$ relies on the differential light absorption of oxygenated hemoglobin, $HbO_2$, and deoxygenated hemoglobin, Hb, to determine their respective concentrations in the arterial blood. Specifically, pulse oximetry measurements are made at red and IR wavelengths chosen such that deoxygenated hemoglobin absorbs more red light than oxygenated hemoglobin, and, conversely, oxygenated hemoglobin absorbs more infrared light than deoxygenated hemoglobin, for example 660 nm (red) and 905 nm (IR).

To distinguish between tissue absorption at the two wavelengths, the red and IR emitters 112 are provided drive current 122 so that only one is emitting light at a given time. For example, the emitters 112 may be cycled on and off alternately, in sequence, with each only active for a quarter cycle and with a quarter cycle separating the active times. This allows for separation of red and infrared signals and removal of ambient light levels by downstream signal processing. Because only a single detector 114 is used, it responds to both the red and infrared emitted light and generates a time-division-multiplexed ("modulated") output signal 124. This modulated signal 124 is coupled to the input of the sensor interface 120.

In addition to the differential absorption of hemoglobin derivatives, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might also comprise skin, muscle, bone, venous blood, fat, pigment, etc., each of which absorbs light. It is generally assumed that the background absorption due to these surrounding tissues is relatively invariant over short time periods and can be easily removed. Thus, blood oxygen saturation measurements are based upon a ratio of the time-varying or AC portion of the detected red and infrared signals with respect to the time-invariant or DC portion:

$$RD/IR = (Red_{AC}/Red_{DC})/(IR_{AC}/IR_{DC})$$

The desired $SpO_2$ measurement is then computed from this ratio. The relationship between RD/IR and $SpO_2$ is most accurately determined by statistical regression of experimental measurements obtained from human volunteers and calibrated measurements of oxygen saturation. In a pulse oximeter device, this empirical relationship can be stored as a "calibration curve" in a read-only memory (ROM) look-up table so that $SpO_2$ can be directly read-out of the memory in response to input RD/IR measurements.

Pulse oximetry is the standard-of-care in various hospital and emergency treatment environments. Demand has lead to pulse oximeters and sensors produced by a variety of manufacturers. Unfortunately, there is no standard for either performance by, or compatibility between, pulse oximeters or sensors. As a result, sensors made by one manufacturer are unlikely to work with pulse oximeters made by another manufacturer. Further, while conventional pulse oximeters and sensors are incapable of taking measurements on patients with poor peripheral circulation and are partially or fully disabled by motion artifact, advanced pulse oximeters and sensors manufactured by the assignee of the present invention are functional under these conditions. This presents a dilemma to hospitals and other caregivers wishing to upgrade their patient oxygenation monitoring capabilities. They are faced with either replacing all of their conventional pulse oximeters, including multiparameter patient monitoring systems, or working with potentially incompatible sensors and inferior pulse oximeters manufactured by various vendors for the pulse oximetry equipment in use at the installation.

Hospitals and other caregivers are also plagued by the difficulty of monitoring patients as they are transported from one setting to another. For example, a patient transported by ambulance to a hospital emergency room will likely be unmonitored during the transition from ambulance to the ER and require the removal and replacement of incompatible sensors in the ER. A similar problem is faced within a hospital as a patient is moved between surgery, ICU and recovery settings. Incompatibility and transport problems are exacerbated by the prevalence of expensive and non-portable multiparameter patient monitoring systems having pulse oximetry modules as one measurement parameter.

One aspect of the present invention is a dual-mode physiological measurement apparatus having a portable mode and an integrated mode. In the integrated mode, the measurement apparatus operates in conjunction with a multiparameter patient monitoring system (MPMS). In the portable mode, the measurement apparatus operates separately from the MPMS. The measurement apparatus has a physiological measurement processor, a display, a MPMS interface and a management processor. The physiological measurement processor has a sensor input and provides a physiological measurement output. In the portable mode, the display indicates a physiological parameter according to the physiological measurement output. In the integrated mode, the MPMS interface provides a communications link between the measurement apparatus and the MPMS. The management processor has as an input the physiological measurement output. The management processor controls the display in the portable mode and communicates the measurement output to the MPMS via the MPMS interface in the integrated mode.

In one embodiment, the measurement apparatus described in the previous paragraph further comprises a plug-in module. The plug-in module comprises the measurement processor and the MPMS interface and possibly the display and management processor and is configured to be removably retained by and electrically connected to the MPMS in the integrated mode. The plug-in module may further comprise a patient cable connector providing the sensor input, a keypad accepting user inputs in the portable mode, and a module connector mating with a corresponding MPMS backplane connector in the integrated mode. In another embodiment, the measurement apparatus further comprises a docking station and a portable portion. The docking station has a docking portion, a plug-in portion and the MPMS interface. The plug-in portion is configured to be removably retained by and electrically connected to the MPMS. The portable portion comprises the measurement processor, the display and the management processor. In the integrated mode, the portable portion is configured to be removably retained by and electrically connected to the docking portion. In the portable mode, the portable portion is separated from the docking station and operated as a standalone patient monitoring apparatus. The portable portion may further comprise a patient cable connector providing the sensor input, a keypad accepting user inputs in the portable mode, and a portable connector mating with a corresponding docking station connector in the integrated mode.

Another aspect of the present invention is a patient monitoring method utilizing a standalone measurement apparatus and a multiparameter patient monitoring system (MPMS) comprising the steps of performing a first physiological measurement with the standalone apparatus physically and electrically isolated from the MPMS and presenting information related to the first measurement on a display portion of the standalone apparatus. Further steps include performing a second physiological measurement with the standalone apparatus interfaced to the MPMS, communicating the second physiological measurement to the MPMS, and presenting information related to the second measurement on a monitor portion of the MPMS.

One embodiment of the patient monitoring method described in the previous paragraph further comprises the step of plugging the measurement apparatus into a module slot portion of the MPMS so that the measurement apparatus is in electrical communications with the MPMS. Another embodiment further comprises the steps of plugging a docking station into a module slot portion of the MPMS so that the docking station is in electrical communications with the MPMS, and attaching the standalone apparatus to the docking station so that the standalone apparatus is in electrical communications with the docking station.

Yet another aspect of the present invention is a physiological measurement apparatus comprising a sensor responsive to a physiological state, a measurement processor means for calculating a physiological parameter based upon the physiological state, which presents the physiological parameter to a person, a packaging means for housing the measurement processor and the display and for providing a connection between the sensor and the measurement processor means, and an interface means for electrically connecting the packaging means to a multiparameter patient monitoring system (MPMS) in an integrated mode and for disconnecting the packaging means from the MPMS in a portable mode. In a particular embodiment, the packaging means comprises a module means for plugging into a slot portion of the MPMS. In another particular embodiment, the physiological measurement apparatus further comprises a docking station means for plugging into a slot portion of the MPMS. In the integrated mode, the packaging means is configured to attach to the docking station.

DETAILED DESCRIPTION

Figure 2:
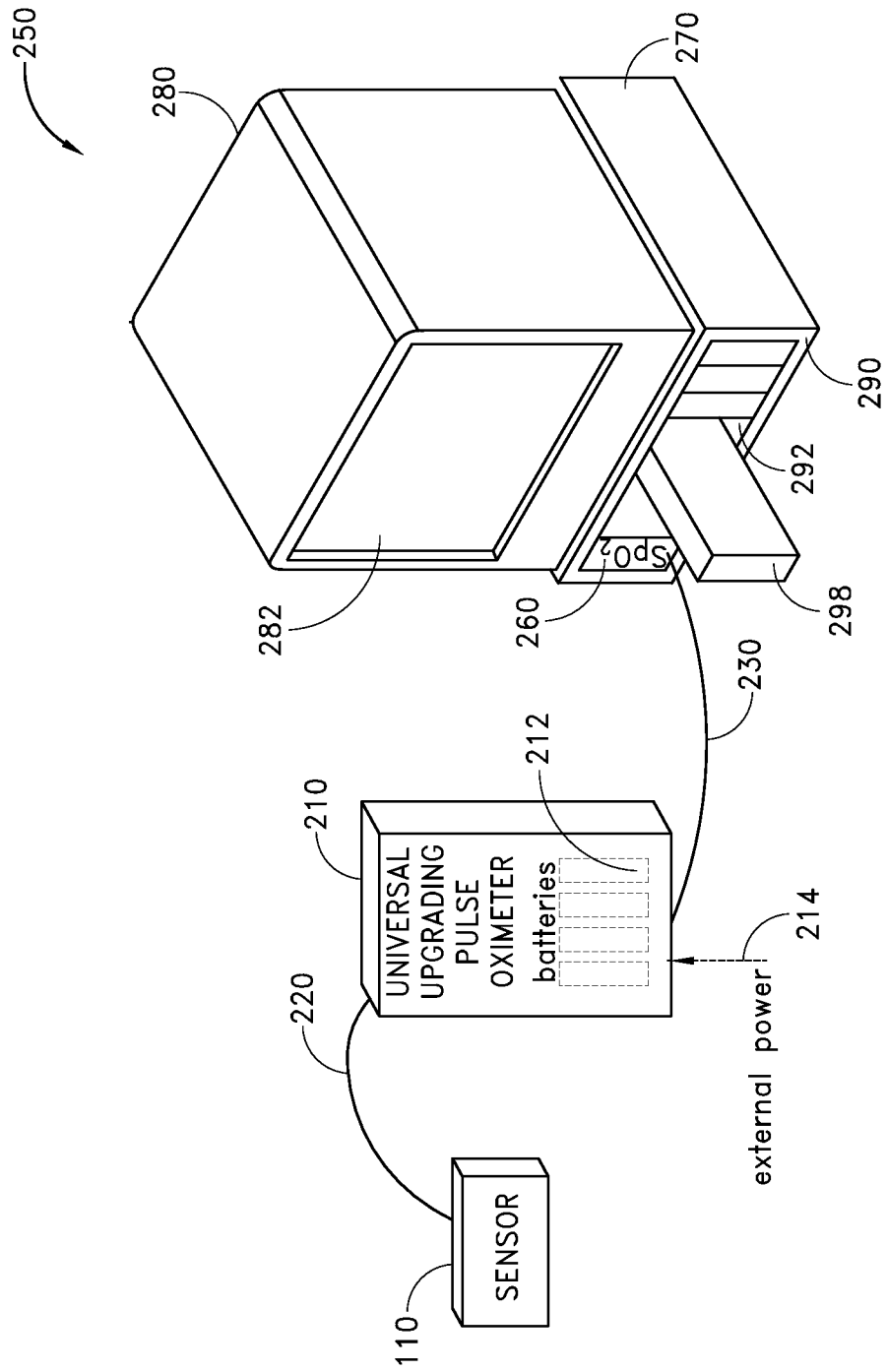
FIG. 2 is a diagram illustrating a patient monitoring system incorporating a universal/upgrading pulse oximeter (UPO) according to the present invention.

FIG. 2 depicts the use of a Universal/Upgrading Pulse Oximeter ("UPO") 210 to perform patient monitoring. A pulse oximetry sensor 110 is attached to a patient (not illustrated) and provides the UPO 210 with a modulated red and IR photo-plethysmograph signal through a patient cable 220. It should be understood that while a pulse oximeter is illustrated, the present invention has applicability to other physiological parameter such as ECG, blood pressure, respiration, etc. The UPO 210 computes the patient's oxygen saturation and pulse rate from the sensor signal and, optionally, displays the patient's oxygen status. The UPO 210 may incorporate an internal power source 212, such as common alkaline batteries or a rechargeable power source. The UPO 210 may also utilize an external power source 214, such as standard 110V AC coupled with an external step-down transformer and an internal or external AC-to-DC converter.

In addition to providing pulse oximetry measurements, the UPO 210 also separately generates a signal, which is received by a pulse oximeter 260 external to the UPO 210. This signal is synthesized from the saturation calculated by the UPO 210 such that the external pulse oximeter 260 calculates the equivalent saturation and pulse rate as computed by the UPO 210. The external pulse oximeter receiving the UPO signal may be a multiparameter patient monitoring system (MPMS) 250 incorporating a pulse oximeter module 260, a standalone pulse oximeter instrument, or any other host instrument capable of measuring $SpO_2$.

As shown in FIG. 2, a MPMS 250 typically has a chassis 270, a multiparameter monitor 280, a processor 1894 (FIG. 18) and a power supply 1892 (FIG. 18), which derives power from a standard external AC power source. The monitor 280 typically incorporates a display 282. The chassis 270 typically has various slots 290 each configured to receive a plug-in module 298. A module connector, e.g. the connector 1750 (FIG. 17B) on the dual-mode pulse oximeter module described with respect to FIGS. 17A-B, below, mates and electrically connects with a corresponding backplane connector (not shown) within the chassis 270. A variety of modules having various patient monitoring functions, such as blood pressure, EKG, respiratory gas and pulse oximetry 260 can be plugged into the slots 290 so that the associated patient parameters can be jointly monitored by the MPMS 250 and logged on the multiparameter display 282.

Also shown in FIG. 2, the UPO 210 is connected to an existing MPMS 250 with a cable 230, advantageously integrating the UPO oxygen status measurements with other MPMS measurements. This allows the UPO calculations to be shown on a unified display of important patient parameters, networked with other patient data, archived within electronic patient records and incorporated into alarm management, which are all MPMS functions convenient to the caregiver.

Figure 3:
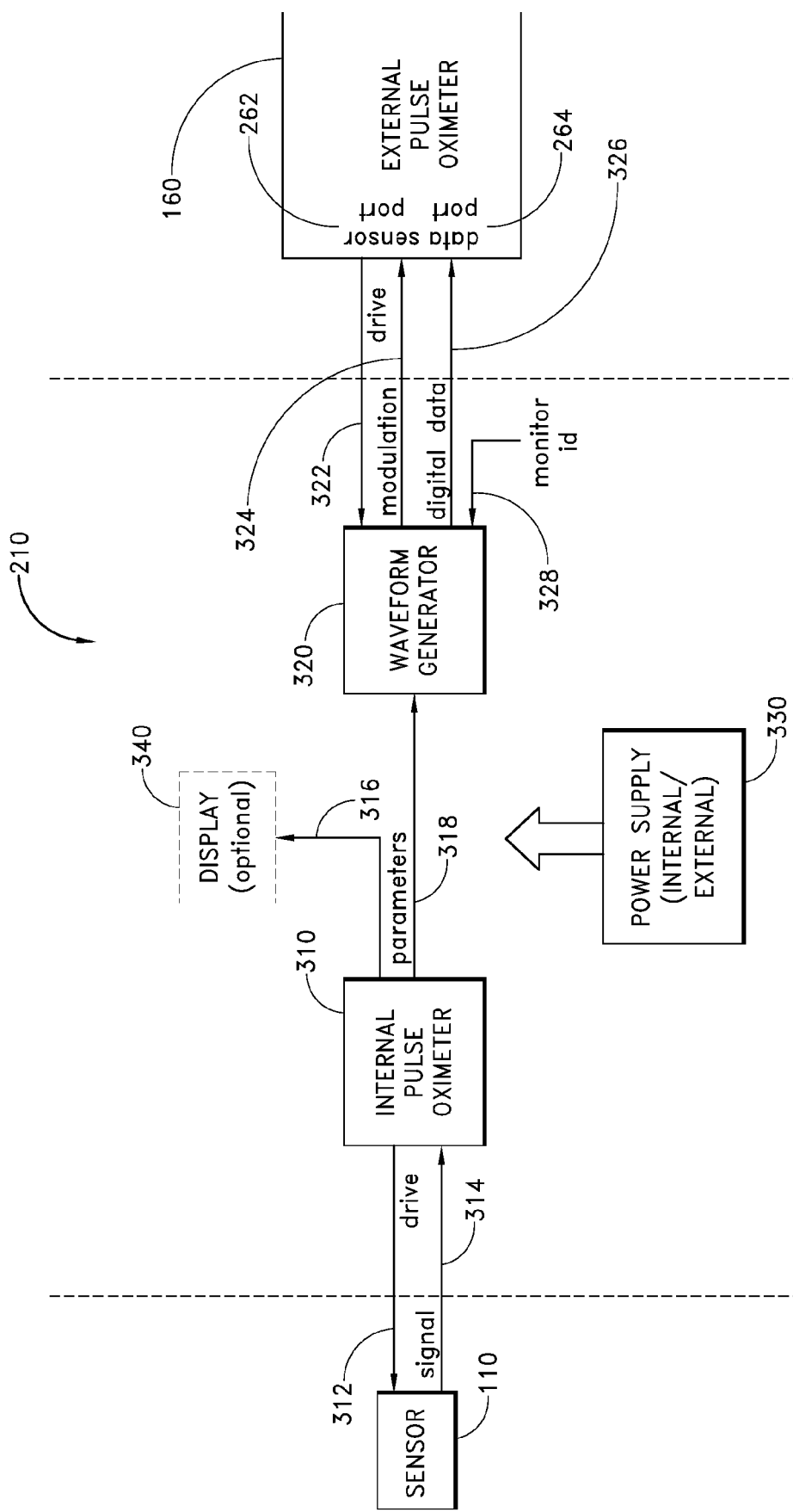
FIG. 3 is top level block diagram of a UPO embodiment.

FIG. 3 depicts a block diagram of the major functions of the UPO 210, including an internal pulse oximeter 310, a waveform generator 320, a power supply 330 and an optional display 340. Attached to the UPO 210 is a sensor 110 and an external pulse oximeter 260. The internal pulse oximeter 310 provides the sensor 110 with a drive signal 312 that alternately activates the sensor's red and IR LEDs, as is known in the art. A corresponding detector signal 314 is received by the internal pulse oximeter 310. The internal pulse oximeter 310 computes oxygen saturation, pulse rate, and, in some embodiments, other physiological parameters such as pulse occurrence, plethysmograph features and measurement confidence. These parameters 318 are output to the waveform generator 320. A portion of these parameters may also be used to generate display drive signals 316 so that patient status may be read from, for example, an LED or LCD display module 340 on the UPO.

The internal pulse oximeter 310 may be a conventional pulse oximeter or, for upgrading an external pulse oximeter 260, it may be an advanced pulse oximeter capable of low perfusion and motion artifact performance not found in conventional pulse oximeters. An advanced pulse oximeter for use as an internal pulse oximeter 310 is described in U.S. Pat. No. 5,632,272 assigned to the assignee of the present invention and incorporated herein by reference. An advanced pulse oximetry sensor for use as the sensor 110 attached to the internal pulse oximeter 310 is described in U.S. Pat. No. 5,638,818 assigned to the assignee of the present invention and incorporated herein by reference. Further, a line of advanced Masimo SET® pulse oximeter OEM boards and sensors are available from the assignee of the present invention.

The waveform generator 320 synthesizes a waveform, such as a triangular waveform having a sawtooth or symmetric triangle shape, that is output as a modulated signal 324 in response to an input drive signal 322. The drive input 322 and modulation output 324 of the waveform generator 320 are connected to the sensor port 262 of the external pulse oximeter 260. The synthesized waveform is generated in a manner such that the external pulse oximeter 260 computes and displays a saturation and a pulse rate value that is equivalent to that measured by the internal pulse oximeter 310 and sensor

110. In the present embodiment, the waveforms for pulse oximetry are chosen to indicate to the external pulse oximeter 260 a perfusion level of 5%. The external pulse oximeter 260, therefore, always receives a strong signal. In an alternative embodiment, the perfusion level of the waveforms synthesized for the external pulse oximeter can be set to indicate a perfusion level at or close to the perfusion level of the patient being monitored by the internal pulse oximeter 310. As an alternative to the generated waveform, a digital data output 326, is connected to the data port 264 of the external pulse oximeter 260. In this manner, saturation and pulse rate measurements and also samples of the unmodulated, synthesized waveform can be communicated directly to the external pulse oximeter 260 for display, bypassing the external pulse oximeter's signal processing functions. The measured plethysmograph waveform samples output from the internal pulse oximeter 310 also may be communicated through the digital data output 326 to the external pulse oximeter 260.

It will be understood from the above discussion that the synthesized waveform is not physiological data from the patient being monitored by the internal pulse oximeter 310, but is a waveform synthesized from predetermined stored waveform data to cause the external pulse oximeter 260 to calculate oxygen saturation and pulse rate equivalent to or generally equivalent (within clinical significance) to that calculated by the internal pulse oximeter 310. The actual physiological waveform from the patient received by the detector is not provided to the external pulse oximeter 260 in the present embodiment. Indeed, the waveform provided to the external pulse oximeter will usually not resemble the plethysmographic waveform of physiological data from the patient being monitored by the internal pulse oximeter 310.

The cable 230 (FIG. 2) attached between the waveform generator 320 and external pulse oximeter 260 provides a monitor ID 328 to the UPO, allowing identification of predetermined external pulse oximeter calibration curves. For example, this cable may incorporate an encoding device, such as a resistor, or a memory device, such as a PROM 1010 (FIG. 10) that is read by the waveform generator 320. The encoding device provides a value that uniquely identifies a particular type of external pulse oximeter 260 having known calibration curve, LED drive and modulation signal characteristics. Although the calibration curves of the external pulse oximeter 260 are taken into account, the wavelengths of the actual sensor 110 need not correspond to the particular calibration curve indicated by the monitor ID 328 or otherwise assumed for the external pulse oximeter 260. That is, the wavelength of the sensor 110 attached to the internal pulse oximeter 310 is not relevant or known to the external pulse oximeter 260.

Figure 4:
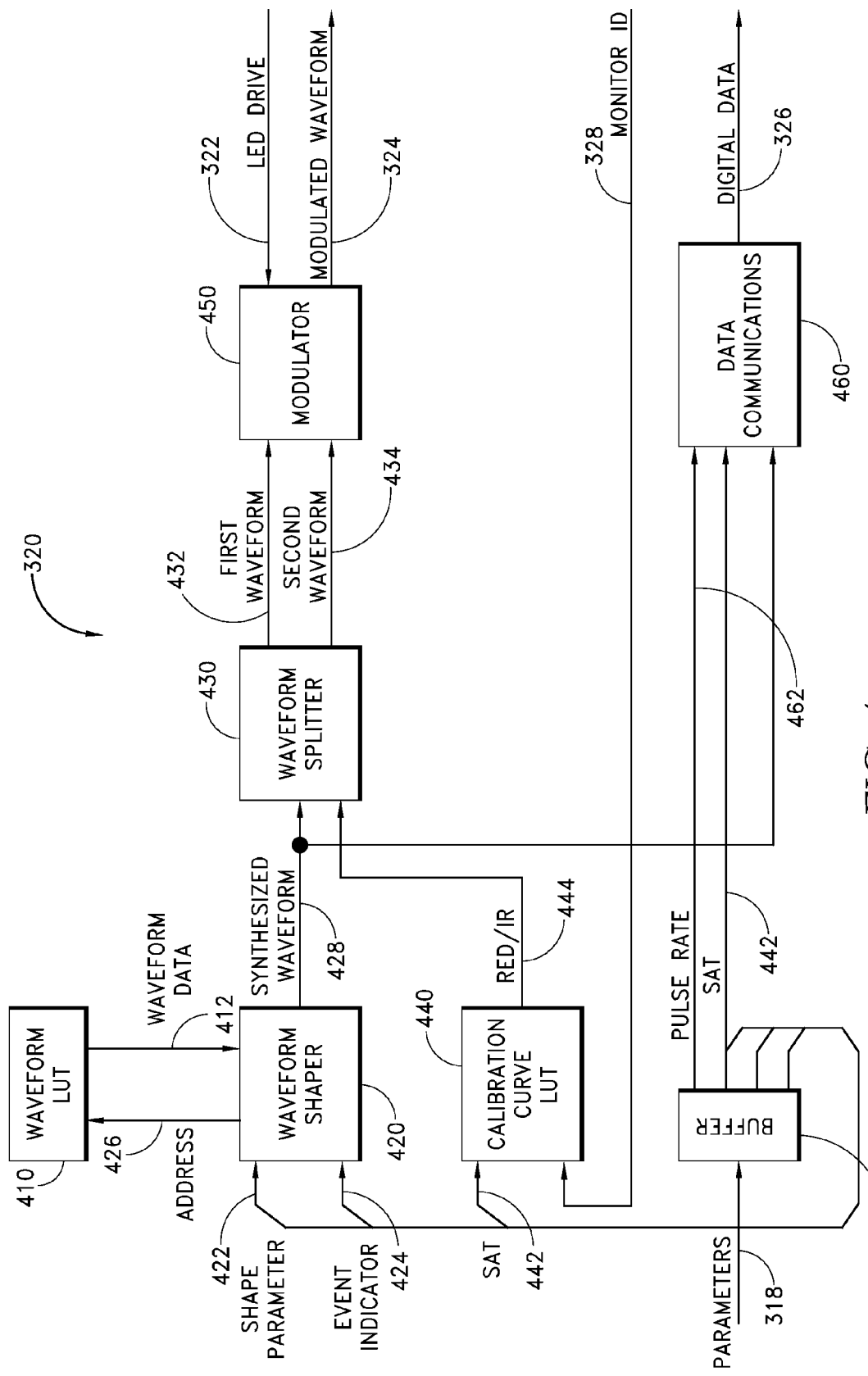
FIG. 4 is a detailed block diagram of the waveform generator portion of the UPO embodiment shown in FIG. 3.

FIG. 4 illustrates one embodiment of the waveform generator portion 320 of the UPO 210 (FIG. 3). Although this illustration may suggest a hardware implementation, the functions of the waveform generator may be implemented in software or firmware or a combination of hardware, software and firmware. The waveform generator 320 performs waveform synthesis with a waveform look-up table ("LUT") 410, a waveform shaper 420 and a waveform splitter 430. The waveform LUT 410 is advantageously a memory device, such as a ROM (read only memory) that contains samples of one or more waveform portions or segments containing a single waveform. These stored waveform segments may be as simple as a single period of a triangular waveform, having a sawtooth or symmetric triangle shape, or more complicated, such as a simulated plethysmographic pulse having various physiological features, for example rise time, fall time and dicrotic notch.

The waveform shaper 420 creates a continuous repeated waveform from the waveform segments provided by the waveform LUT 410. The waveform shaper 420 has a shape parameter input 422 and an event indicator input 424 that are buffered 470 from the parameters 318 output from the internal pulse oximeter 310 (FIG. 3). The shape parameter input 422 determines a particular waveform segment in the waveform LUT 410. The chosen waveform segment is specified by the first address transmitted to the waveform LUT 410 on the address lines 426. The selected waveform segment is sent to the waveform shaper 420 as a series of samples on the waveform data lines 412.

The event indicator input 424 specifies the occurrence of pulses in the plethysmograph waveform processed by the internal pulse oximeter 310 (FIG. 3). For example, the event indicator may be a delta time from the occurrence of a previously detected falling pulse edge or this indicator could be a real time or near real time indicator or flag of the pulse occurrence. The waveform shaper 420 accesses the waveform LUT 410 to create a corresponding delta time between pulses in the synthesized waveform output 428. In one embodiment, the waveform shaper is clocked at a predetermined sample rate. From a known number of samples per stored waveform segment and the input delta time from the event indicator, the waveform shaper 420 determines the number of sequential addresses to skip between samples and accesses the waveform LUT 410 accordingly. This effectively "stretches" or "shrinks" the retrieved waveform segment so as to fit in the time between two consecutive pulses detected by the UPO.

The waveform splitter 430 creates a first waveform 432 corresponding to a first waveform (such a red wavelength) expected by the external pulse oximeter 260 (FIG. 3) and a second waveform (such as infrared) 434 expected by the external pulse oximeter 260. The relative amplitudes of the first waveform 432 and second waveform 434 are adjusted to correspond to the ratio output 444 from a calibration curve LUT 440. Thus, for every value of measured oxygen saturation at the sat input 442, the calibration curve LUT 440 provides a corresponding ratio output 444 that results in the first waveform 432 and the second waveform 434 having an amplitude ratio that will be computed by the external pulse oximeter 260 (FIG. 3) as equivalent to the oxygen saturation measured by the internal pulse oximeter 310 (FIG. 3).

As described above, one particularly advantageous aspect of the UPO is that the operating wavelengths of the sensor 110 (FIG. 3) are not relevant to the operating wavelengths required by the external pulse oximeter 260 (FIG. 3), i.e. the operating wavelengths that correspond to the calibration curve or curves utilized by the external pulse oximeter. The calibration curve LUT 440 simply permits generation of a synthesized waveform as expected by the external oximeter 260 (FIG. 3) based on the calibration curve used by the external pulse oximeter 260 (FIG. 3). The calibration curve LUT 440 contains data about the known calibration curve of the external pulse oximeter 260 (FIG. 3), as specified by the monitor ID input 328. In other words, the waveform actually synthesized is not a patient plethysmographic waveform. It is merely a stored waveform that will cause the external pulse oximeter to calculate the proper oxygen saturation and pulse rate values. Although this does not provide a patient plethysmograph on the external pulse oximeter for the clinician, the calculated saturation and pulse rate values, which is what is actually sought, will be accurate.

A modulator 450 responds to an LED drive input 322 from the external pulse oximeter to generate a modulated waveform output 324 derived from the first waveform 432 and second waveform 434. Also, a data communication interface 460 transmits as a digital data output 326 the data obtained from the sat 442, pulse rate 462 and synthesized waveform 428 inputs.

Figure 5:
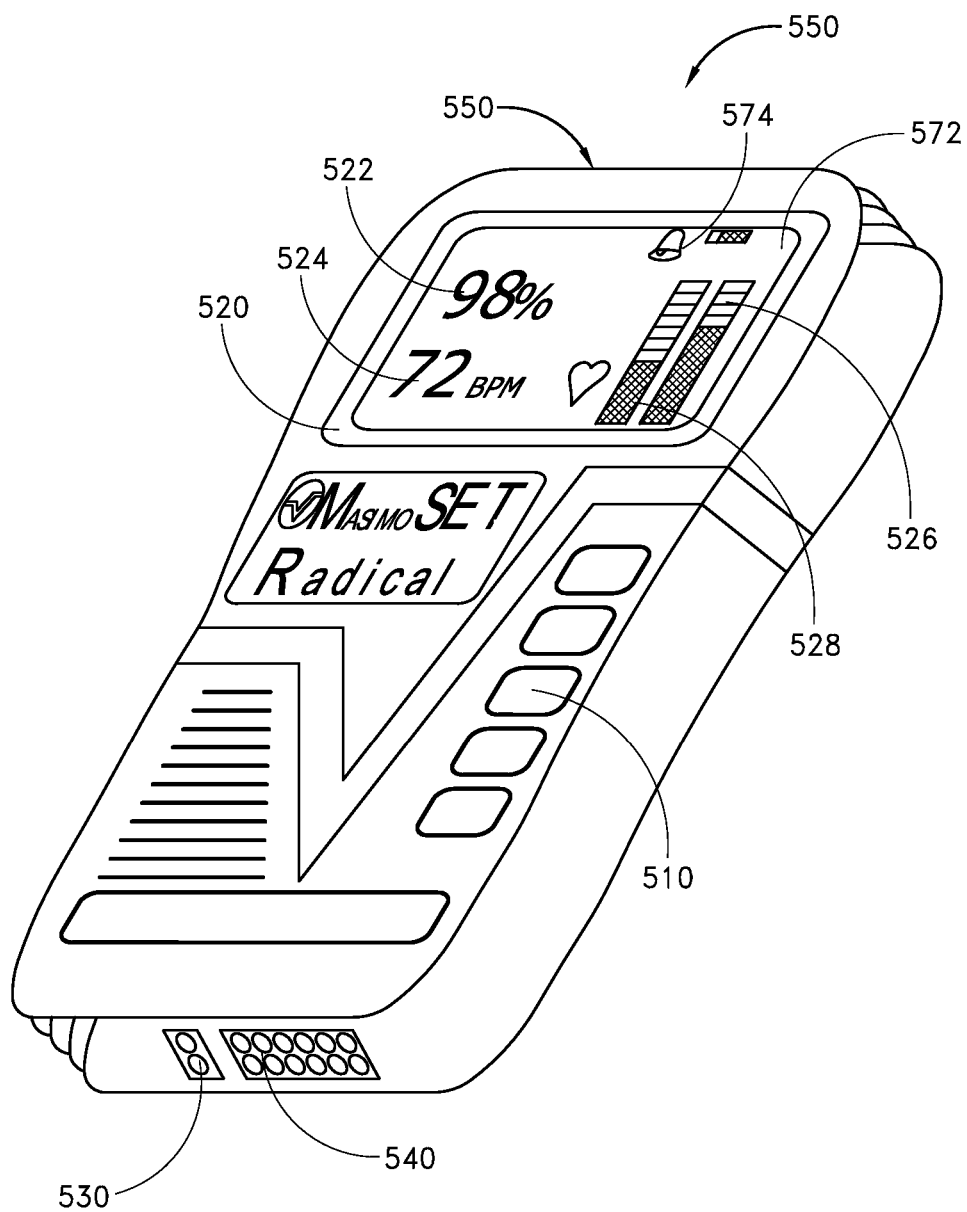
FIG. 5 is an illustration of a handheld embodiment of the UPO.

FIG. 5 depicts a handheld UPO 500 embodiment. The handheld UPO 500 has keypad inputs 510, an LCD display 520, an external power supply input 530, an output port 540 for connection to an external pulse oximeter and a sensor input 550 at the top edge (not visible). The display 520 shows the measured oxygen saturation 522, the measured pulse rate 524, a pulsating bar 526 synchronized with pulse rate or pulse events, and a confidence bar 528 indicating confidence in the measured values of saturation and pulse rate. Also shown are low battery 572 and alarm enabled 574 status indicators.

The handheld embodiment described in connection with FIG. 5 may also advantageously function in conjunction with a docking station that mechanically accepts, and electrically connects to, the handheld unit. The docking station may be co-located with a patient monitoring system and connected to a corresponding $SpO_2$ module sensor port, external power supply, printer and telemetry device, to name a few options. In this configuration, the handheld UPO may be removed from a first docking station at one location to accompany and continuously monitor a patient during transport to a second location. The handheld UPO can then be conveniently placed into a second docking station upon arrival at the second location, where the UPO measurements are displayed on the patient monitoring system at that location.

Figure 6:
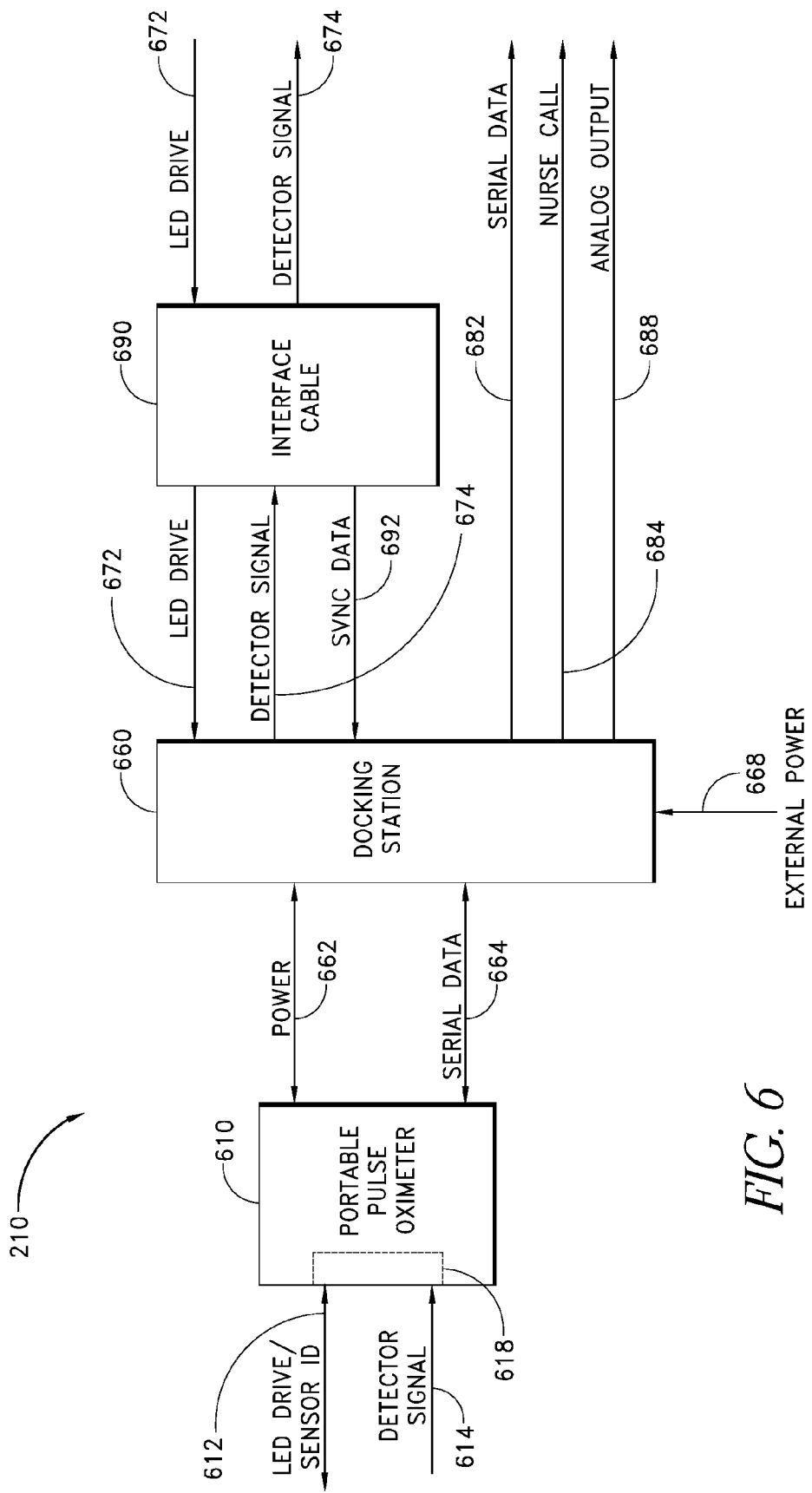
FIG. 6 is a top level block diagram of another UPO embodiment incorporating a portable pulse oximeter and a docking station.

FIG. 6 shows a block diagram of a UPO embodiment, where the functions of the UPO 210 are split between a portable pulse oximeter 610 and a docking station 660. The portable pulse oximeter 610 ("portable") is a battery operated, fully functional, stand-alone pulse oximeter instrument. The portable 610 connects to a sensor 110 (FIG. 2) through a UPO patient cable 220 (FIG. 2) attached to a patient cable connector 618. The portable 610 provides the sensor 110 with a drive signal 612 that alternately activates the sensor's red and IR LEDs, as is well-known in the art. The portable also receives a corresponding detector signal 614 from the sensor. The portable can also input a sensor ID on the drive signal line 612, as described in U.S. Pat. No. 5,758,644 entitled Manual and Automatic Probe Calibration, assigned to the assignee of the present invention and incorporated herein by reference.

The portable 610 can be installed into the docking station 660 to expand its functionality. When installed, the portable 610 can receive power 662 from the docking station 660 if the docking station 660 is connected to external power 668. Alternately, with no external power 668 to the docking station 660, the portable 610 can supply power 662 to the docking station 660. The portable 610 communicates to the docking station with a bidirectional serial data line 664. In particular, the portable 610 provides the docking station with $SpO_2$, pulse rate and related parameters computed from the sensor detector signal 614. When the portable 610 is installed, the docking station 660 may drive a host instrument 260 (FIG. 2) external to the portable 610. Alternatively, the portable 610 and docking station 660 combination may function as a standalone pulse oximeter instrument, as described below with respect to FIG. 13.

In one embodiment, the docking station 660 does not perform any action when the portable 610 is not docked. The user interface for the docking station 660, i.e. keypad and display, is on the portable 610 in the present embodiment. An indicator LED on the docking station 660 is lit when the portable is docked. The docking station 660 generates a detector signal output 674 to the host instrument 260 (FIG. 2) in response to LED drive signals 672 from the host instrument and $SpO_2$ values and related parameters, received from the portable 610. The docking station 660 also provides a serial data output 682, a nurse call 684 and an analog output 688.

An interface cable 690 connects the docking station 660 to the host instrument. The LED drive signals 672 and detector signal output 674 are communicated between the docking station 660 and the host instrument 260 (FIG. 2) via the interface cable 690. The interface cable 690 provides a sync data output 692 to the docking station 660, communicating sensor, host instrument (e.g. monitor ID 328, FIG. 3) and calibration curve data. Advantageously, this data allows the docking station 660 to provide signals to a particular host instrument on which it can operate.

Figure 7:
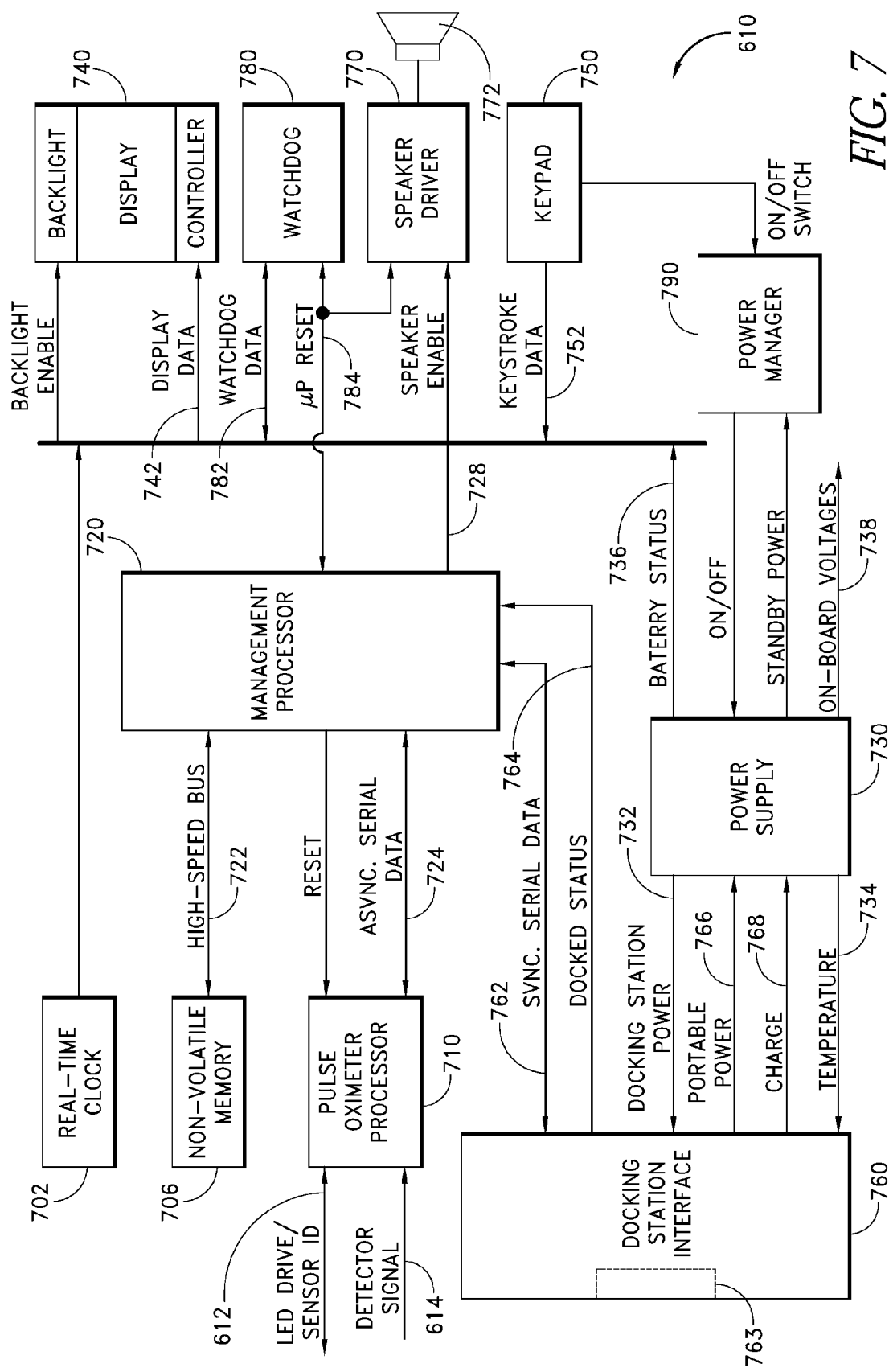
FIG. 7 is a detailed block diagram of the portable pulse oximeter portion of FIG. 6.

FIG. 7 provides further detail of the portable 610. The portable components has a pulse oximeter processor 710, a management processor 720, a power supply 730, a display 740 and a keypad 750. The pulse oximeter processor 710 functions as an internal pulse oximeter, interfacing the portable to a sensor 110 (FIG. 2) and deriving $SpO_2$, pulse rate, a plethysmograph and a pulse indicator. An advanced pulse oximeter for use as the pulse oximeter processor 710 is described in U.S. Pat. No. 5,632,272, referenced above. An advanced pulse oximetry sensor for use as the sensor 110 (FIG. 2) attached to the pulse oximeter processor 710 is described in U.S. Pat. No. 5,638,818, also referenced above. Further, a line of advanced Masimo SET® pulse oximeter OEM boards and sensors are available from the assignee of the present invention. In one embodiment, the pulse oximeter processor 710 is the Masimo SET® MS-3L board or a low power MS-5 board available from Masimo Corporation.

The management processor 720 controls the various functions of the portable 610, including asynchronous serial data communications 724 with the pulse oximeter processor 710 and synchronous serial communications 762 with the docking station 660 (FIG. 6). The physical and electrical connection to the docking station 660 (FIG. 6) is via a docking station connector 763 and the docking station interface 760, respectively. The processor 720 utilizes a real-time clock 702 to keep the current date and time, which includes time and date information that is stored along with $SpO_2$ parameters to create trend data. In one embodiment, the processor of the portable 610 and the docking station 660 (FIG. 6) can be from the same family of processors to share common routines and minimize code development time.

Figure 8:
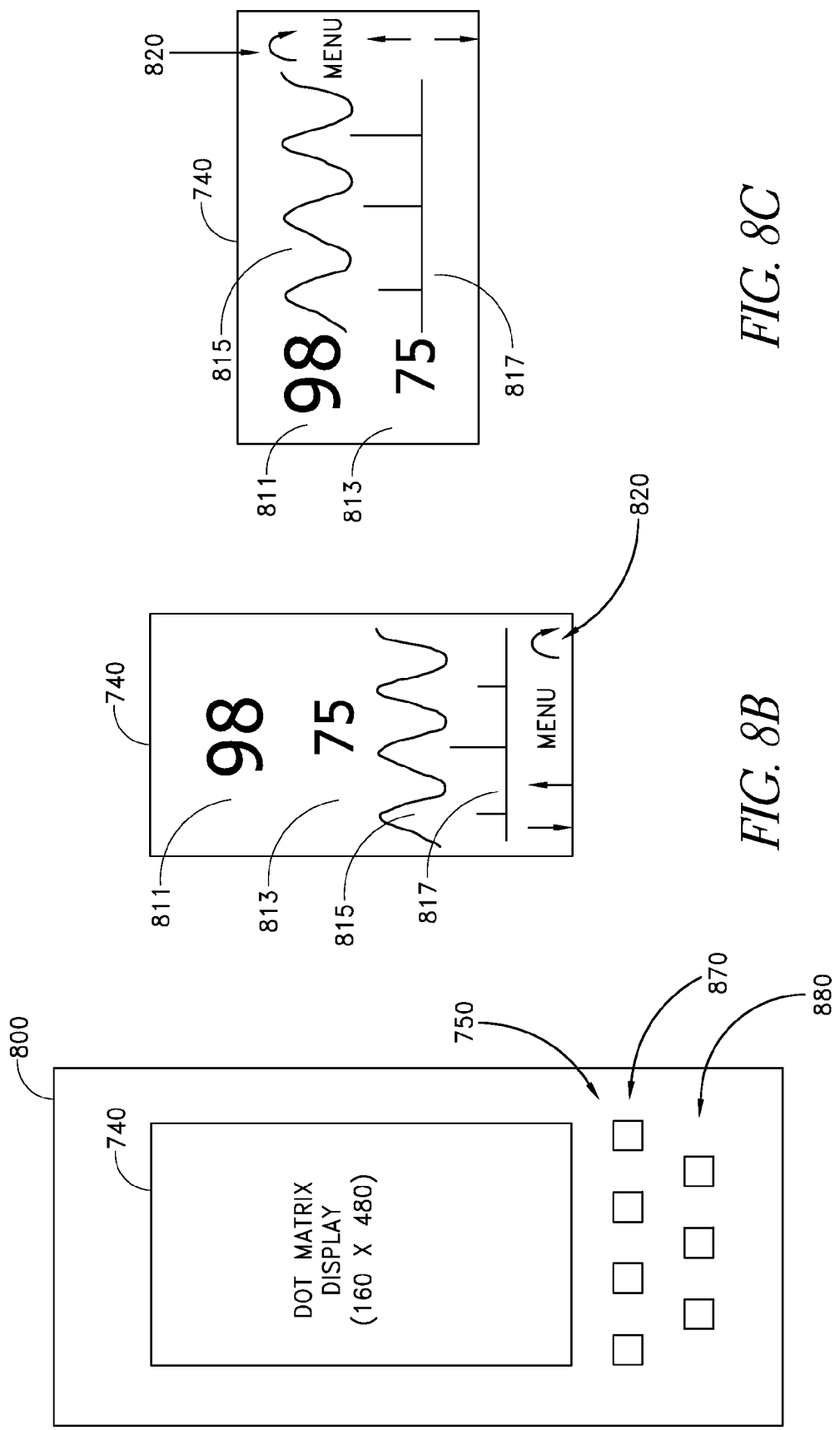
FIG. 8A is an illustration of the portable pulse oximeter user interface, including a keyboard and display.
FIGS. 8B-C are illustrations of the portable pulse oximeter display showing portrait and landscape modes, respectively.

The processor 720 also controls the user interface 800 (FIG. 8A) by transferring display data 742 to the display 740, including display updates and visual alarms, and by interpreting keystroke data 752 from the keypad 750. The processor 720 generates various alarm signals, when required, via an enable signal 728, which controls a speaker driver 770. The speaker driver 770 actuates a speaker 772, which provides audible indications such as, for example, alarms and pulse beeps. The processor 720 also monitors system status, which includes battery status 736, indicating battery levels, and docked status 764, indicating whether the portable 610 is connected to the docking station 660 (FIG. 6). When the portable 610 is docked and is on, the processor 720 also decides when to turn on or off docking station power 732.

Advantageously, the caregiver can set (i.e. configure or program) the behavior of the portable display 740 and alarms when the docked portable 610 senses that an interface cable 690 has connected the docking station 660 to an external pulse oximeter, such as a multiparameter patient monitoring system. In one user setting, for example, the portable display 740 stops showing the $SpO_2$ 811 (FIG. 8) and pulse rate 813 (FIG. 8) values when connected to an external pulse oximeter to avoid confusing the caregiver, who can read equivalent values on the patient monitoring system. The display 740, however, continues to show the plethysmograph 815 (FIG. 8) and visual pulse indicator 817 (FIG. 8) waveforms. For one such user setting, the portable alarms remain active.

Another task of the processor 720 includes maintenance of a watchdog function. The watchdog 780 monitors processor status on the watchdog data input 782 and asserts the µP reset output 784 if a fault is detected. This resets the management processor 720, and the fault is indicated with audible and visual alarms.

The portable 610 gets its power from batteries in the power supply 730 or from power 766 supplied from the docking station 660 (FIG. 6) via the docking station interface 760. A power manager 790 monitors the on/off switch on the keypad 750 and turns-on the portable power accordingly. The power manager 790 turns off the portable on command by the processor 720. DC/DC converters within the power supply 730 generate the required voltages 738 for operation of the portable 610 and docking station power 732. The portable batteries are preferably rechargeable batteries or another renewable power source. The batteries of the power supply 730 supply docking station power 732 when the docking station 660 (FIG. 6) is without external power. A battery charger within the docking station power supply provides charging current 768 to rechargeable batteries within the power supply 730. The docking station power supply 990 (FIG. 9) monitors temperature 734 from a thermistor in the rechargeable battery pack, providing an indication of battery charge status.

A non-volatile memory 706 is connected to the management processor 720 via a high-speed bus 722. In the present embodiment, the memory 706 is an erasable and field reprogrammable device used to store boot data, manufacturing serial numbers, diagnostic failure history, adult $SpO_2$ and pulse rate alarm limits, neonate $SpO_2$ and pulse rate alarm limits, $SpO_2$ and pulse rate trend data, and program data. Other types of non-volatile memory are well known. The $SpO_2$ and pulse rate alarm limits, as well as $SpO_2$ related algorithm parameters, may be automatically selected based on the type of sensor 110 (FIG. 2), adult or neonate, connected to the portable 610.

The LCD display 740 employs LEDs for a backlight to increase its contrast ratio and viewing distance when in a dark environment. The intensity of the backlight is determined by the power source for the portable 610. When the portable 610 is powered by either a battery pack within its power supply 730 or a battery pack in the docking station power supply 990 (FIG. 9), the backlight intensity is at a minimum level. When the portable 610 is powered by external power 668 (FIG. 6), the backlight is at a higher intensity to increase viewing distance and angle. In one embodiment, a button on the portable permits overriding these intensity settings, and provides adjustment of the intensity. The backlight is controlled in two ways. Whenever any key is pressed, the backlight is illuminated for a fixed number of seconds and then turns off, except when the portable is docked and derives power from an external source. In that case, the backlight is normally on unless deactivated with a key on the portable 610.

FIG. 8A illustrates the portable user interface 800, which includes a display 740 and a keypad 750. In one embodiment, the display 740 is an LCD device having 160 pixels by 480 pixels. The display 740 can be shown in portrait mode, illustrated in FIG. 8B, or in landscape mode, illustrated in FIG. 8C. A tilt (orientation) sensor 950 (FIG. 9) in the docking station 660 (FIG. 6) or a display mode key on the portable 610 (FIG. 6) determines portrait or landscape mode. The tilt sensor 950 (FIG. 9) can be a gravity-activated switch or other device responsive to orientation and can be alternatively located in the portable 610 (FIG. 6). In a particular embodiment, the tilt sensor 950 (FIG. 9) is a non-mercury tilt switch, part number CW 1300-1, available from Comus International, Nutley, N.J. (www.comus-intl.com). The tilt sensor 950 (FIG. 9) could also be a mercury tilt switch.

Examples of how the display area can be used to display $SpO_2$ 811, pulse rate 813, a plethysmographic waveform 815, a visual pulse indicator 817 and soft key icons 820 in portrait and landscape mode are shown in FIGS. 8B and 8C, respectively. The software program of the management processor 720 (FIG. 7) can be easily changed to modify the category, layout and size of the display information shown in FIGS. 8B-C. Other advantageous information for display is $SpO_2$ limits, alarm limits, alarm disabled, exception messages and battery status.

The keypad 750 includes soft keys 870 and fixed keys 880. The fixed keys 880 each have a fixed function. The soft keys 870 each have a function that is programmable and indicated by one of the soft key icons 820 located next to the soft keys 870. That is, a particular one of the soft key icons 820 is in proximity to a particular one of the soft keys 870 and has a text or a shape that suggests the function of that particular one of the soft keys 870. In one embodiment, the button portion of each key of the keypad 750 is constructed of florescent material so that the keys 870, 880 are visible in the dark.

In one embodiment, the keypad 750 has one row of four soft keys 870 and one row of three fixed keys 880. Other configurations are, of course, available, and specific arrangement is not significant. In one embodiment, the functions of the three fixed keys 880 are power, alarm silence and light/contrast. The power function is an on/off toggle button. The alarm silence function and the light/contrast function have dual purposes depending on the duration of the key press. A momentary press of the key corresponding to the alarm silence function will disable the audible alarm for a fixed period of time. To disable the audible alarm indefinitely, the key corresponding to the alarm silence function is held down for a specified length of time. If the key corresponding to the alarm silence function is pressed while the audible alarm has been silenced, the audible alarm is reactivated. If the key corresponding to the light/contrast function is pressed momentarily, it is an on/off toggle button for the backlight. If the key corresponding to the light/contrast function is held down, the display contrast cycles through its possible values.

In the present embodiment, the default functions of the four soft keys 870 are pulse beep up volume, pulse beep down volume, menu select, and display mode. These functions are indicated on the display by the up arrow, down arrow, "menu" and curved arrow soft key icons 820, respectively. The up volume and down volume functions increase or decrease the audible sound or "beep" associated with each detected pulse. The display mode function rotates the display 740 through all four orthogonal orientations, including portrait mode (FIG. 8B) and landscape mode (FIG. 8C), with each press of the corresponding key. The menu select function allows the functionality of the soft keys 870 to change from the default functions described above. Examples of additional soft key functions that can be selected using this menu feature are set $SpO_2$ high/low limit, set pulse rate high/low limit, set alarm volume levels, set display to show trend data, print trend data, erase trend data, set averaging time, set sensitivity mode, perform synchronization, perform rechargeable battery maintenance (deep discharge/recharge to remove battery memory), and display product version number.

Figure 9:
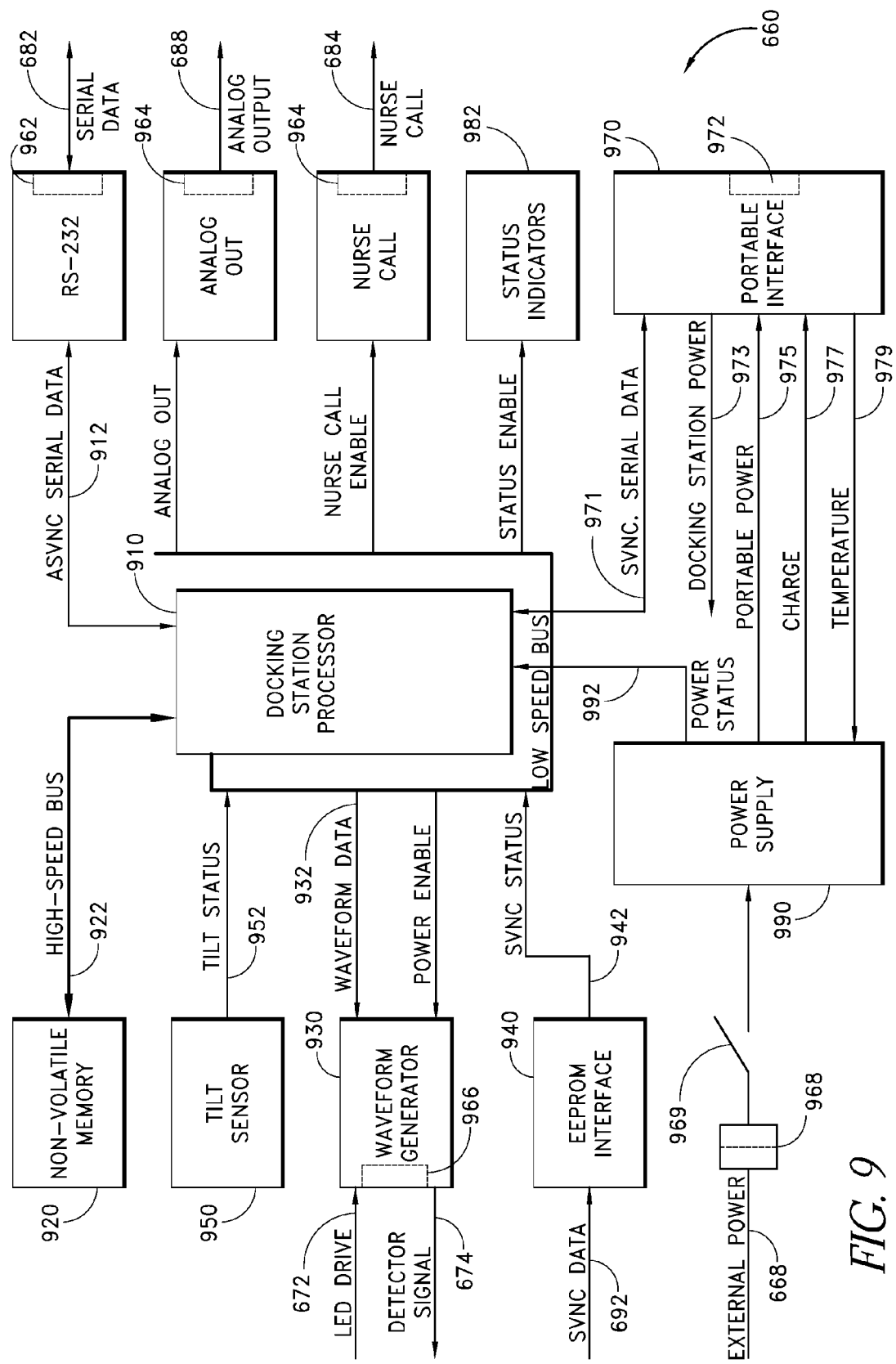
FIG. 9 is a detailed block diagram of the docking station portion of FIG. 6.

FIG. 9 provides further details of the docking station 660, which includes a docking station processor 910, a non-volatile memory 920, a waveform generator 930, a PROM interface 940, a tilt sensor 950, a portable interface 970 and associated connector 972, status indicators 982, a serial data port 682, a nurse call output 684, an analog output 688 and a power supply 990. In one embodiment, the docking station 660 is intended to be associated with a fixed (non-transportable) host instrument, such as a multiparameter patient monitoring instrument in a hospital emergency room. In a transportable embodiment, the docking station 660 is movable, and includes a battery pack within the power supply 990.

The docking station processor 910 orchestrates the activity on the docking station 660. The processor 910 provides the waveform generator 930 with parameters 932 as discussed above for FIGS. 3 and 4. The processor 910 also provides asynchronous serial data 912 for communications with external devices and synchronous serial data 971 for communications with the portable 610 (FIG. 6). In addition, the processor 910 determines system status including sync status 942, tilt status 952 and power status 992. The portable management processor 720 (FIG. 7) performs the watchdog function for the docking station processor 910. The docking station processor 910 sends watchdog messages to the portable processor 720 (FIG. 7) as part of the synchronous serial data 972 to ensure the correct operation of the docking station processor 910.

The docking station processor 910 can also perform resource downloading to the portable processor 720 (FIG. 7) as part of the synchronous serial data 971. That is, the docking station 660 can provide functionality not present in the portable 610 (FIG. 6), and, when docked, that added capability can be reflected by the portable user interface, i.e. the soft keys 870 (FIG. 8A) and the display 740 (FIG. 8A). For example, a portable 610 (FIG. 6) providing only pulse oximetry measurements can be docked to a docking station 660 having the added functionality of blood pressure measurements. The docking station 660 can download a blood pressure measurement menu and an associated user interface to the portable 610 (FIG. 6) upon docking, allowing the portable 610 (FIG. 6) to control and display this additional docking station functionality. Docking station resource downloading would apply to other physiological measurements as well, such as respiration rate, EEG, ECG and $EtCO_2$ to name a few.

The docking station processor 910 accesses non-volatile memory 920 over a high-speed bus 922. The non-volatile memory 920 is re-programmable and contains program data for the processor 910 including instrument communication protocols, synchronization information, a boot image, manufacturing history and diagnostic failure history.

The waveform generator 930 generates a synthesized waveform that a conventional pulse oximeter can process to calculate $SpO_2$ and pulse rate values or exception messages, as described above with respect to FIG. 4. However, in the present embodiment, as explained above, the waveform generator output does not reflect a physiological waveform. It is merely a waveform constructed from stored memory data to cause the external pulse oximeter to calculate the correct saturation and pulse rate. In an alternative arrangement, physiological data could be scaled or otherwise mathematically converted and provided to the external pulse oximeter, but the external pulse oximeter would often not be able to calculate the proper saturation values, and the upgrading feature would be lost. This is particularly true due to the likely mismatch in the actual sensor wavelength and the calibration curves in the external pulse oximeter. The waveform generator 930 is enabled if an interface cable 690 (FIG. 6), described below with respect to FIG. 10, with valid synchronization information is connected. Otherwise, the power to the waveform generator 930 is disabled, thereby rendering the waveform generator inoperable.

The status indicators 982 are a set of LEDs on the front of the docking station 660 used to indicate various conditions including external power (AC), portable docked, portable battery charging, docking station battery charging and alarm. The serial data port 682 is used to interface with either a computer, a serial port of conventional pulse oximeters or serial printers via a standard RS-232 DB-9 connector 962. This port 682 can output trend memory, $SpO_2$ and pulse rate and support the system protocols of various manufacturers. The analog output 688 is used to interface with analog input chart recorders via a connector 964 and can output "real-time" or trend $SpO_2$ and pulse rate data. The nurse call output 684 from a connector 964 is activated when alarm limits are exceeded for a predetermined number of consecutive seconds. In another embodiment, data, including alarms, could be routed to any number of communications ports, and even over the Internet, to permit remote use of the upgrading pulse oximeter.

The PROM interface 940 accesses synchronization data 692 from the PROM 1010 (FIG. 10) in the interface cable 690 (FIGS. 6, 10) and provides synchronization status 942 to the docking station processor 910. The portable interface 970 provides the interconnection to the portable 610 (FIG. 6) through the docking station interface 760 (FIG. 7).

As shown in FIG. 9, external power 668 is provided to the docking station 660 through a standard AC connector 968 and on/off switch 969. When the docking station 660 has external power 668, the power supply 990 charges the battery in the portable power supply 730 (FIG. 7) and the battery, if any, in the docking station power supply 990. When the portable 610 (FIG. 6) is either removed or turned off, the docking station power 973 is removed and the docking station 660 is turned off, except for the battery charger portion of the power supply 990. The docking station power 973 and, hence, the docking station 660 powers on whenever a docked portable 610 (FIG. 6) is switched on. The portable 610 (FIG. 6) supplies power for an embodiment of the docking station 660 without a battery when external power 668 is removed or fails.

Figure 10:
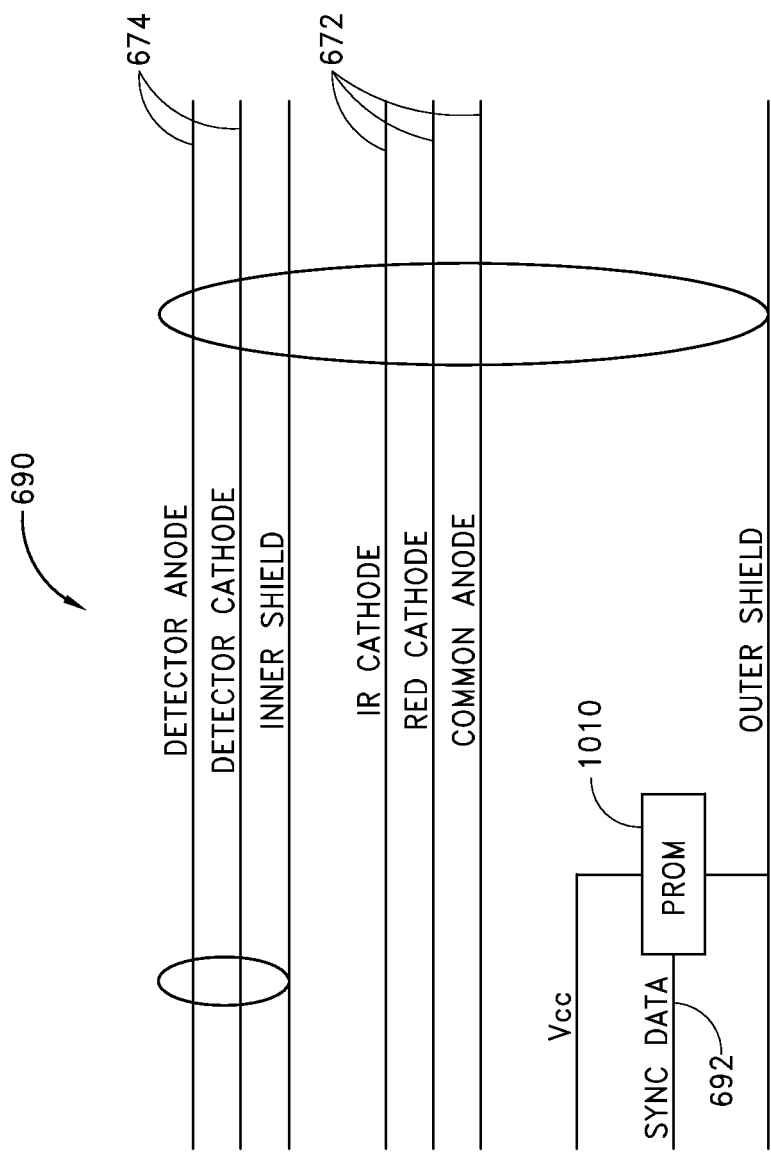
FIG. 10 is a schematic of the interface cable portion of FIG. 6.

FIG. 10 provides further detail regarding the interface cable 690 used to connect between the docking station 660 (FIG. 6) and the host instrument 260 (FIG. 2). The interface cable 690 is configured to interface to a specific host instrument via the sensor input to the host instrument. A PROM 1010 built into the interface cable 690 contains information identifying a sensor type, a specific host instrument, and the calibration data (if necessary) of the specific host instrument. This PROM information can be read by the docking station 660 (FIG. 6) as synchronization data 692. Advantageously, the synchronization data 692 allows the docking station 660 (FIG. 6) to generate a waveform to the host instrument that causes the host instrument to display $SpO_2$ values equivalent to those calculated by the portable 610 (FIG. 6). The interface cable 690 includes an LED drive path 672. In the embodiment shown in FIG. 10, the LED drive path 672 is configured for common anode LEDs and includes IR cathode, red cathode and common anode signals. The interface cable 690 also includes a detector drive path 674, including detector anode and detector cathode signals.

A menu option on the portable 610 (FIG. 6) also allows synchronization information to be calculated in the field. With manual synchronization, the docking station 660 (FIG. 6) generates a waveform to the host instrument 260 (FIG. 2) and displays an expected $SpO_2$ value. The user enters into the portable the $SpO_2$ value displayed on the host instrument using the portable keypad 750 (FIG. 7). These steps are repeated until a predetermined number of data points are entered and the SpO₂ values displayed by the portable and the host instrument are consistent.

Figure 11A:
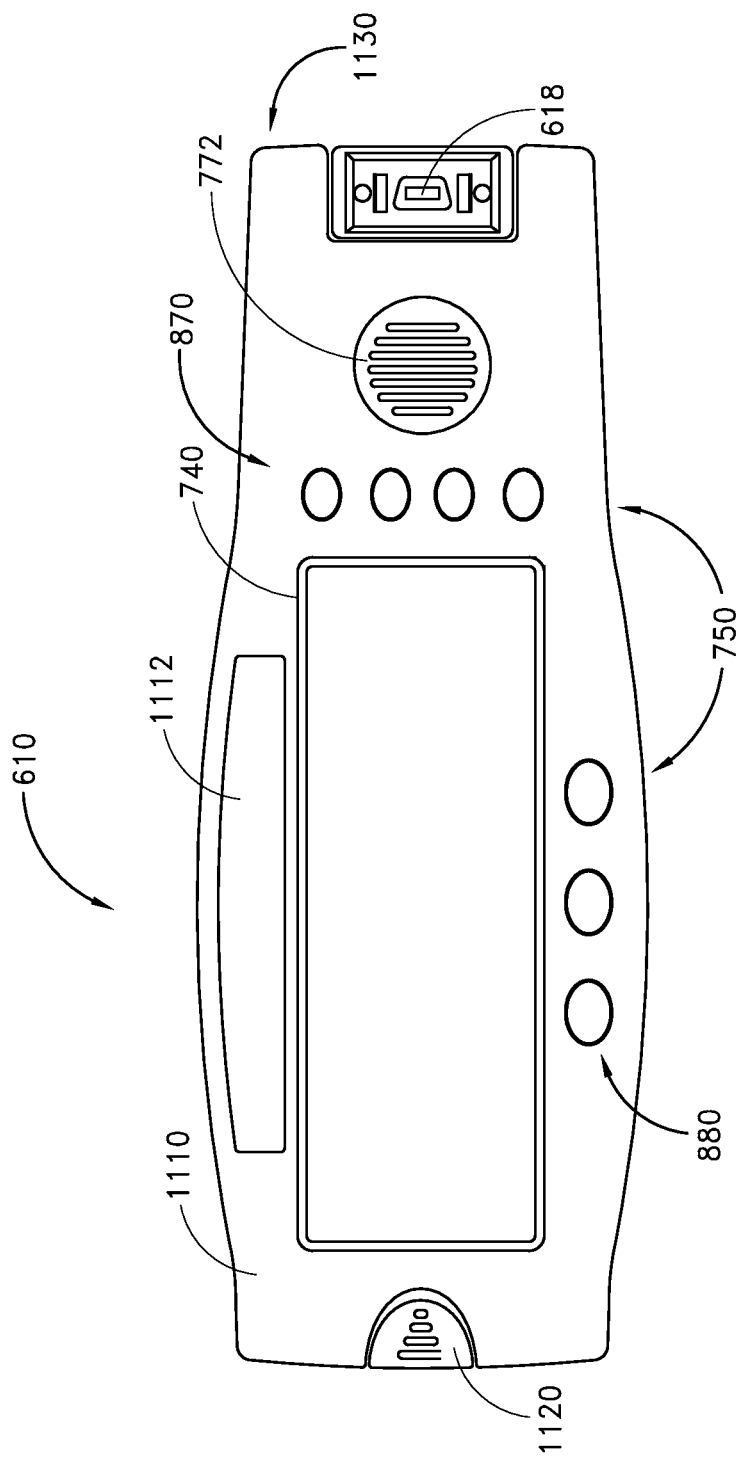
FIG. 11A is a front view of an embodiment of a portable pulse oximeter.
Figure 11B:
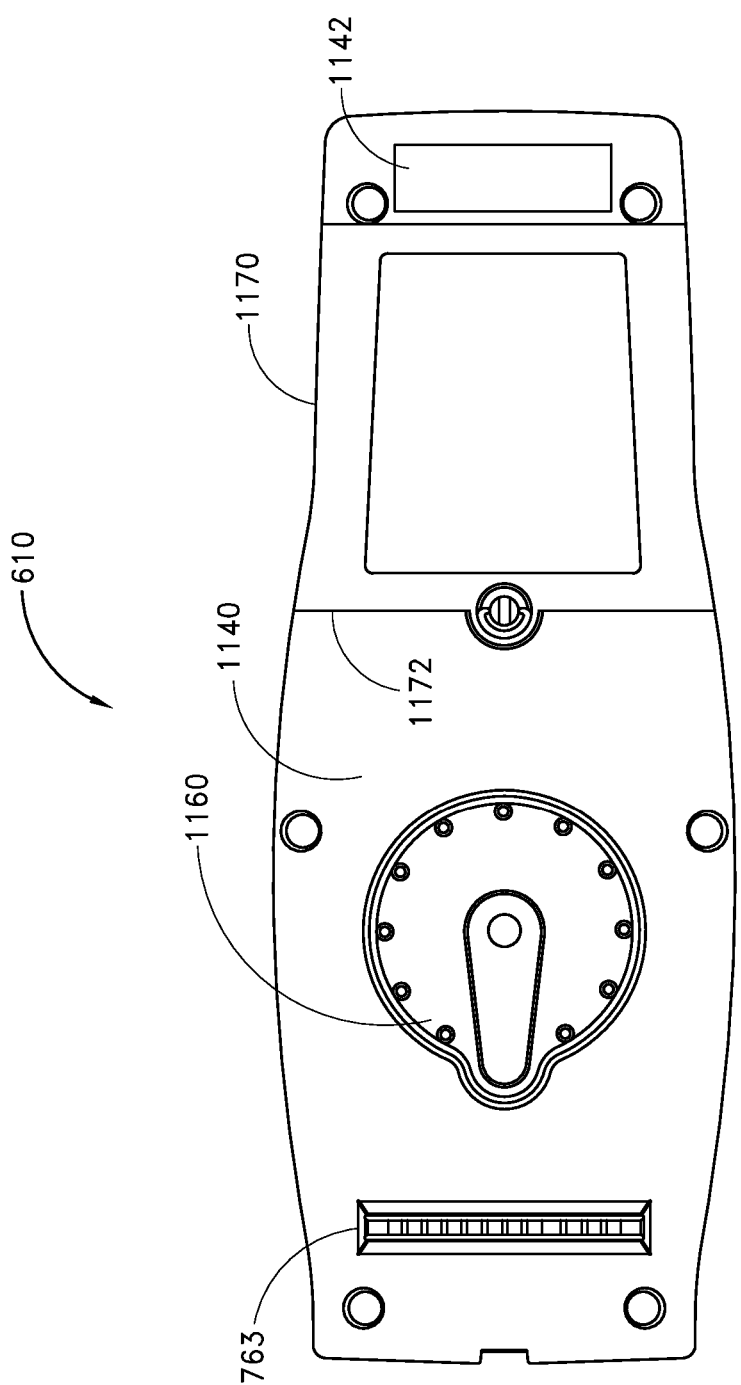
FIG. 11B is a back view of a portable pulse oximeter.
Figure 12A:
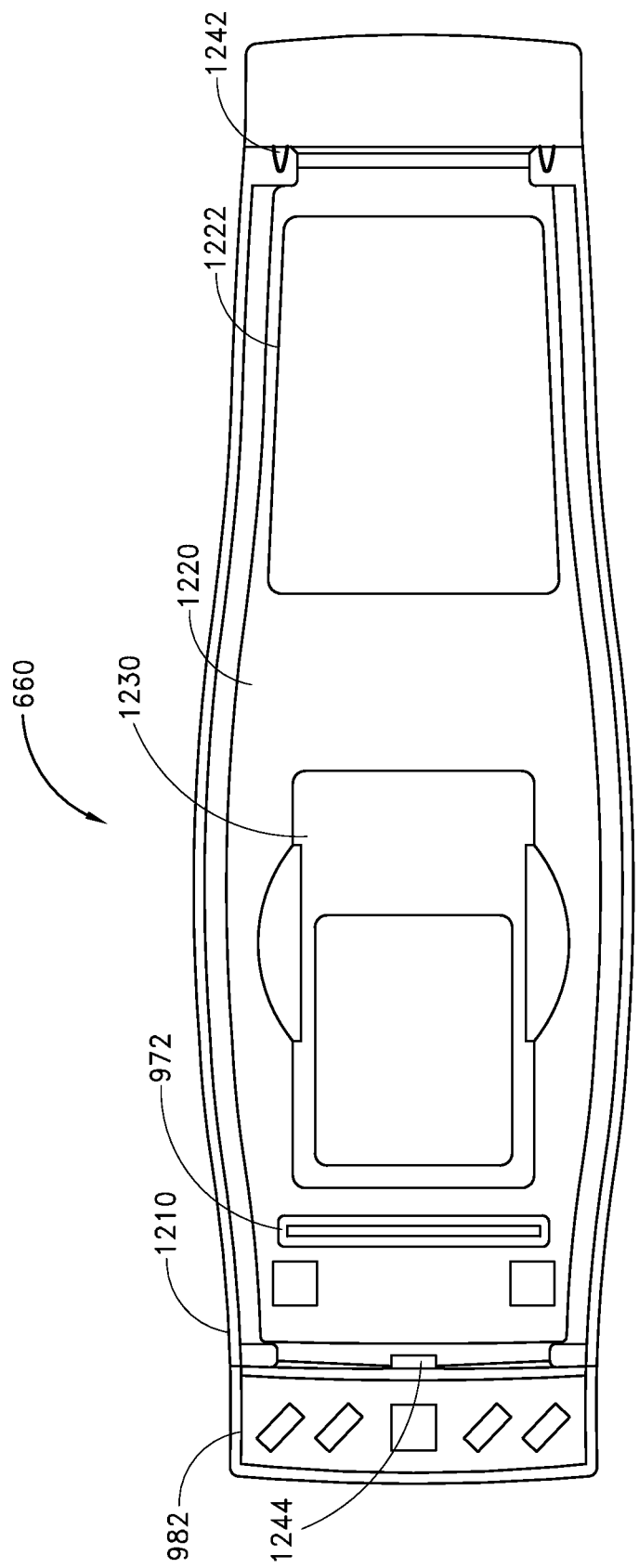
FIG. 12A is a front view of an embodiment of a docking station.
Figure 12B:
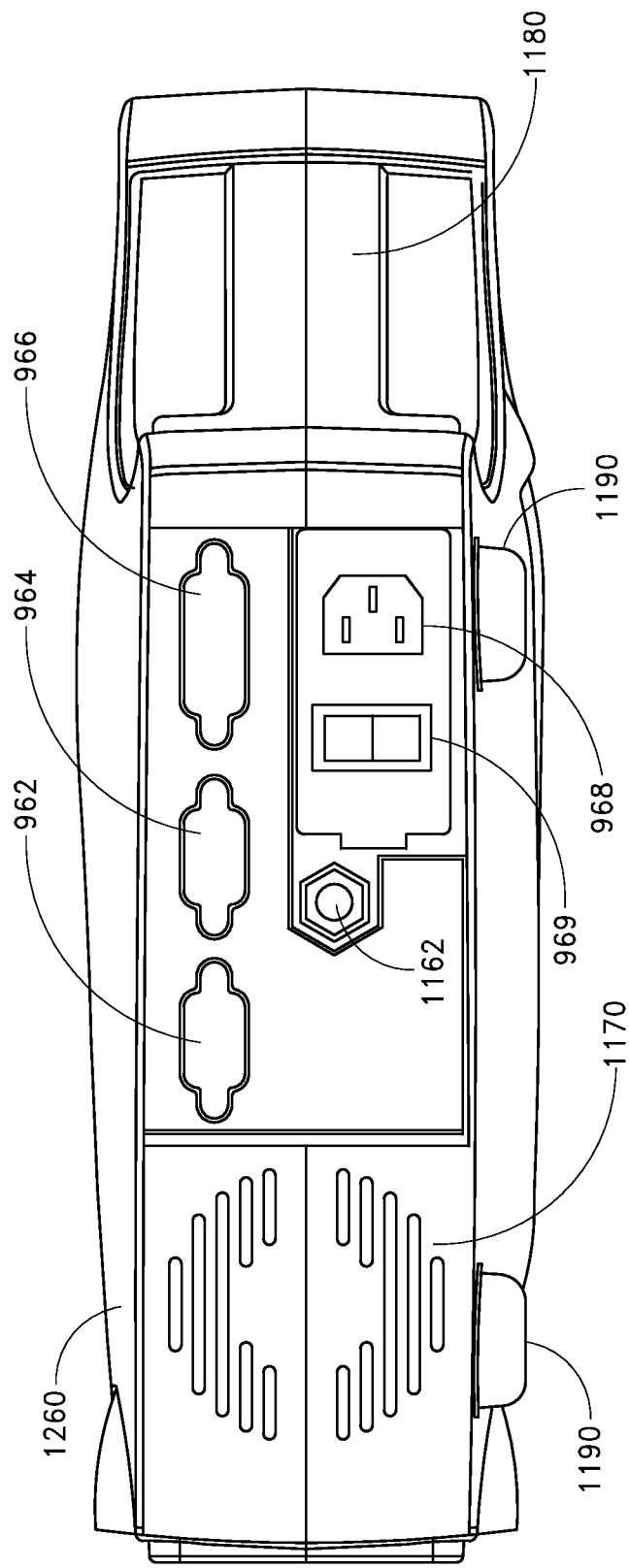
FIG. 12B is a back view of a docking station.
Figure 13:
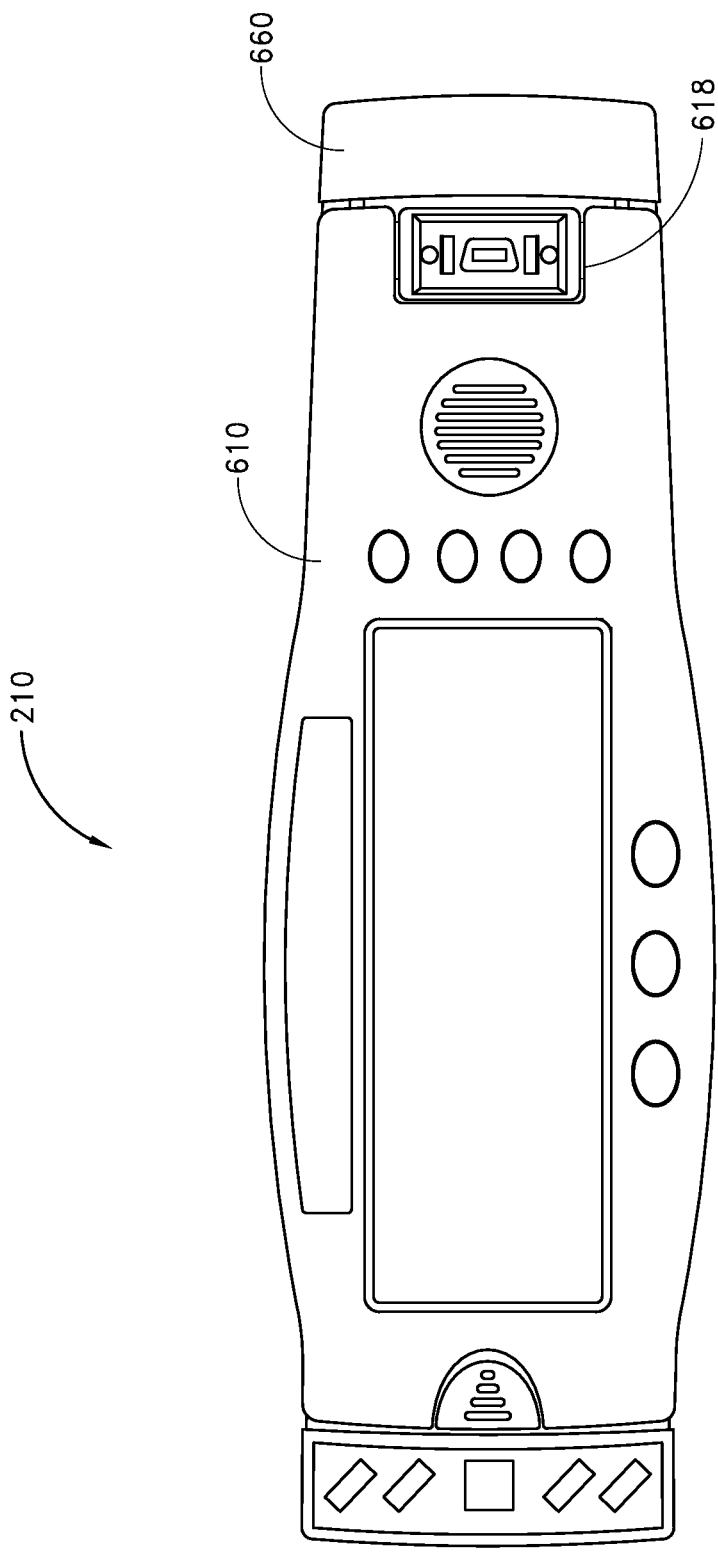
FIG. 13 is a front view of a portable docked to a docking station.

FIGS. 11A-B depict an embodiment of the portable 610, as described above with respect to FIG. 6. FIGS. 12A-B depict an embodiment of the docking station 660, as described above with respect to FIG. 6. FIG. 13 depicts an embodiment of the UPO 210 where the portable 610 is docked with the docking station 660, also as described above with respect to FIG. 6.

FIG. 11A depicts the portable front panel 1110. The portable 610 has a patient cable connector 618, as described above with respect to FIG. 6. Advantageously, the connector 618 is rotatably mounted so as to minimize stress on an attached patient cable (not shown). In one embodiment, the connector 618 can freely swivel between a plane parallel to the front panel 1110 and a plane parallel to the side panel 1130. In another embodiment, the connector 618 can swivel between, and be releasably retained in, three semi-locked positions. The connector 618 can be rotated from a semi-locked position with moderate force. A first locked position is as shown, where the connector is in a plane parallel to the front panel 1110. A second locked position is where the connector 618 is in a plane parallel to the side panel 1130. The connector 618 also has an intermediate locked position 45° between the first and the second locked positions. The connector 618 is placed in the first locked position for attachment to the docking station 660.

Shown in FIG. 11A, the portable front panel 1110 also has a speaker 772, as described with respect to FIG. 7. Further, the front panel 1110 has a row of soft keys 870 and fixed keys 880, as described above with respect to FIG. 8. In addition, the front panel 1110 has a finger actuated latch 1120 that locks onto a corresponding catch 1244 (FIG. 12A) in the docking station 660, allowing the portable 610 to be releasably retained by the docking station 660. An OEM label can be affixed to a recessed area 1112 on the front panel 1110.

FIG. 11B depicts the portable back panel 1140. The back panel 1140 has a socket 763, a pole clamp mating surface 1160, and a battery pack compartment 1170. The socket 763 is configured to mate with a corresponding docking station plug 972 (FIG. 12A). The socket 763 and plug 972 (FIG. 12A) provide the electrical connection interface between the portable 610 and the docking station 660 (FIG. 12A). The socket 763 houses multiple spring contacts that compress against plated edge-connector portions of the docking station plug 972 (FIG. 12A). A conventional pole clamp (not shown) may be removably attached to the mating surface 1160. This conveniently allows the portable 610 to be held to various patient-side or bedside mounts for hands-free pulse oximetry monitoring. The portable power supply 730 (FIG. 7) is contained within the battery pack compartment 1170. The compartment 1170 has a removable cover 1172 for protection, insertion and removal of the portable battery pack. Product labels, such as a serial number identifying a particular portable, can be affixed with the back panel indent 1142.

Figure 1:
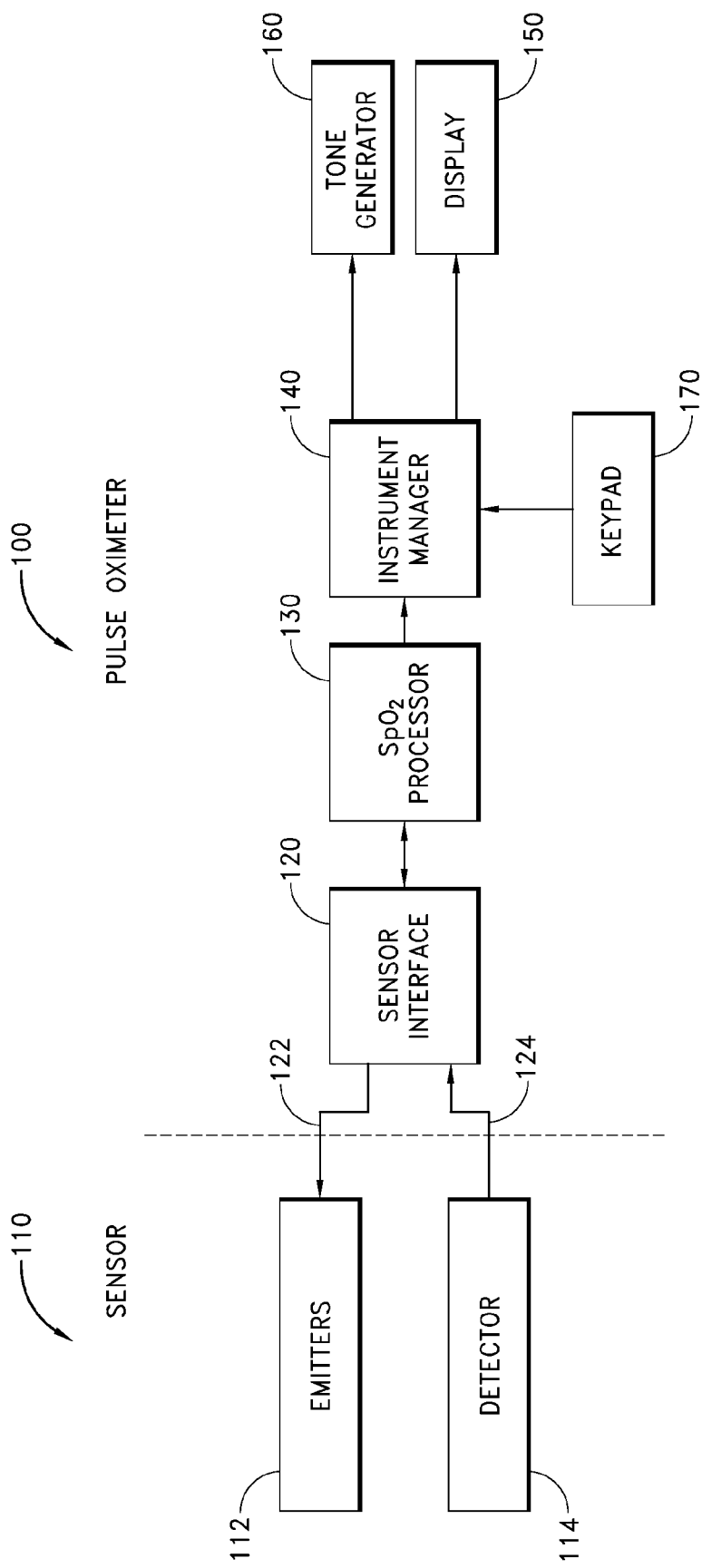
FIG. 1 is a block diagram of a prior art pulse oximeter.

FIG. 12A depicts the front side 1210 of the docking station 660. The front side 1210 has a docking compartment 1220, a pole clamp recess 1230, pivots 1242, a catch 1244, a plug connector 972 and LED status indicators 982. The docking compartment 1220 accepts and retains the portable 610 (FIGS. 11A-B), as shown in FIG. 13. When the portable 610 (FIGS. 11A-B) is docked in the compartment 1220, the:pole clamp recess 1230 accommodates a pole clamp (not shown) attached to the portable's pole clamp mating surface 1160 (FIG. 11B), assuming the pole clamp is in its closed position. The portable 610 (FIGS. 11A-B) is retained in the compartment 1220 by pivots 1242 that fit into corresponding holes in the portable's side face 1130 and a catch 1244 that engages the portable's latch 1120 (FIG. 11A). Thus, the portable 610 (FIGS. 11A-B) is docked by first attaching it at one end to the pivots 1242, then rotating it about the pivots 1242 into the compartment 1220, where it is latched in place on the catch 1244. The portable 610 (FIGS. 11A-B) is undocked in reverse order, by first pressing the latch 1120 (FIG. 11A), which releases the portable from the catch 1244, rotating the portable 610 (FIGS. 11A-B) about the pivots 1242 out of the compartment 1220 and then removing it from the pivots 1242. As the portable is rotated into the compartment, the docking station plug 972 inserts into the portable socket 763 (FIG. 1B), providing the electrical interface between the portable 610 and the docking station 660. The status indicators 982 are as described above with respect to FIG. 9.

FIG. 12B depicts the back side 1260 of the docking station 660. The back side 1260 has a serial (RS-232 or USB) connector 962, an analog output and nurse call connector 964, an upgrade port connector 966, an AC power plug 968, an on/off switch 969 and a ground lug 1162. A handle 1180 is provided at one end and fan vents 1170 are provided at the opposite end. A pair of feet 1190 are visible near the back side 1260. A corresponding pair of feet (not visible) are located near the front side 1210 (FIG. 12A). The feet near the front side 1210 extend so as to tilt the front side 1210 (FIG. 12A) upward, making the display 740 (FIG. 13) of a docked portable 610 (FIG. 13) easier to read.

FIG. 13 illustrates both the portable 610 and the docking station 660. The portable 610 and docking station 660 constitute three distinct pulse oximetry instruments. First, the portable 610 by itself, as depicted in FIGS. 11A-B, is a handheld pulse oximeter applicable to various patient monitoring tasks requiring battery power or significant mobility, such as ambulance and ER situations. Second, the portable 610 docked in the docking station 660, as depicted in FIG. 13, is a standalone pulse oximeter applicable to a wide-range of typical patient monitoring situations from hospital room to the operating room. Third, the portable 610 docked and the upgrade port 966 (FIG. 12B) connected with an interface cable to the sensor port of a conventional pulse oximeter module 260 (FIG. 2) within a multiparameter patient monitoring instrument 250 (FIG. 2) or other conventional pulse oximeter, is a universal/upgrading pulse oximeter (UPO) instrument 210, as described herein. Thus, the portable 610 and docking station 660 configuration of the UPO 210 advantageously provides a three-in-one pulse oximetry instrument functionality.

Another embodiment of the docking station 660 incorporates an input port that connects to a blood pressure sensor and an output port that connects to the blood pressure sensor port of a multiparameter patient monitoring system (MPMS). The docking station 660 incorporates a signal processor that computes a blood pressure measurement based upon an input from the blood pressure sensor. The docking station 660 also incorporates a waveform generator connected to the output port that produces a synthesized waveform based upon the computed measurement. The waveform generator output is adjustable so that the blood pressure value displayed on the MPMS is equivalent to the computed blood pressure measurement. Further, when the portable 610 is docked in the docking station 660 and the blood pressure sensor is connected to the input port, the portable displays a blood pressure value according to the computed blood pressure measurement. Thus, in this embodiment, the docking station 660 provides universal/upgrading capability for both blood pressure and SpO₂.

Likewise, the docking station 660 can function as an universal/upgrading instrument for other vital sign measurements, such as respiratory rate, EKG or EEG. For this embodiment, the docking station 660 incorporates related sensor connectors and associated sensor signal processors and upgrade connectors to an MPMS or standalone instrument. In this manner, a variety of vital sign measurements can be incorporated into the docking station 660, either individually or in combination, with or without $SpO_2$ as a measurement parameter, and with or without the portable 610. In yet another embodiment, the docking station 660 can be configured as a simple $SpO_2$ upgrade box, incorporating a $SpO_2$ processor and patient cable connector for an $SpO_2$ sensor that functions with or without the portable 610.

Unlike a conventional standalone pulse oximeter, the standalone configuration shown in FIG. 13 has a rotatable display 740 that allows the instrument to be operated in either a vertical or horizontal orientation. A tilt sensor 950 (FIG. 9) indicates when the bottom face 1310 is placed along a horizontal surface or is otherwise horizontally-oriented. In this horizontal orientation, the display 740 appears in landscape mode (FIG. 8C). The tilt sensor 950 (FIG. 9) also indicates when the side face 1320 is placed along a horizontal surface or is otherwise horizontally oriented. In this vertical orientation, the display 740 appears in portrait mode (FIG. 8B). A soft key 870 on the portable 610 can override the tilt sensor, allowing the display to be presented at any 90° orientation, i.e. portrait, landscape, "upside-down" portrait or "upside-down" landscape orientations. The handheld configuration (FIG. 11A), can also present the display 740 at any 90° orientation using a soft key 870. In the particular embodiment described above, however, the portable 610 does not have a separate tilt sensor and, hence, relies on a soft key 870 to change the orientation of the display when not docked.

Figure 14:
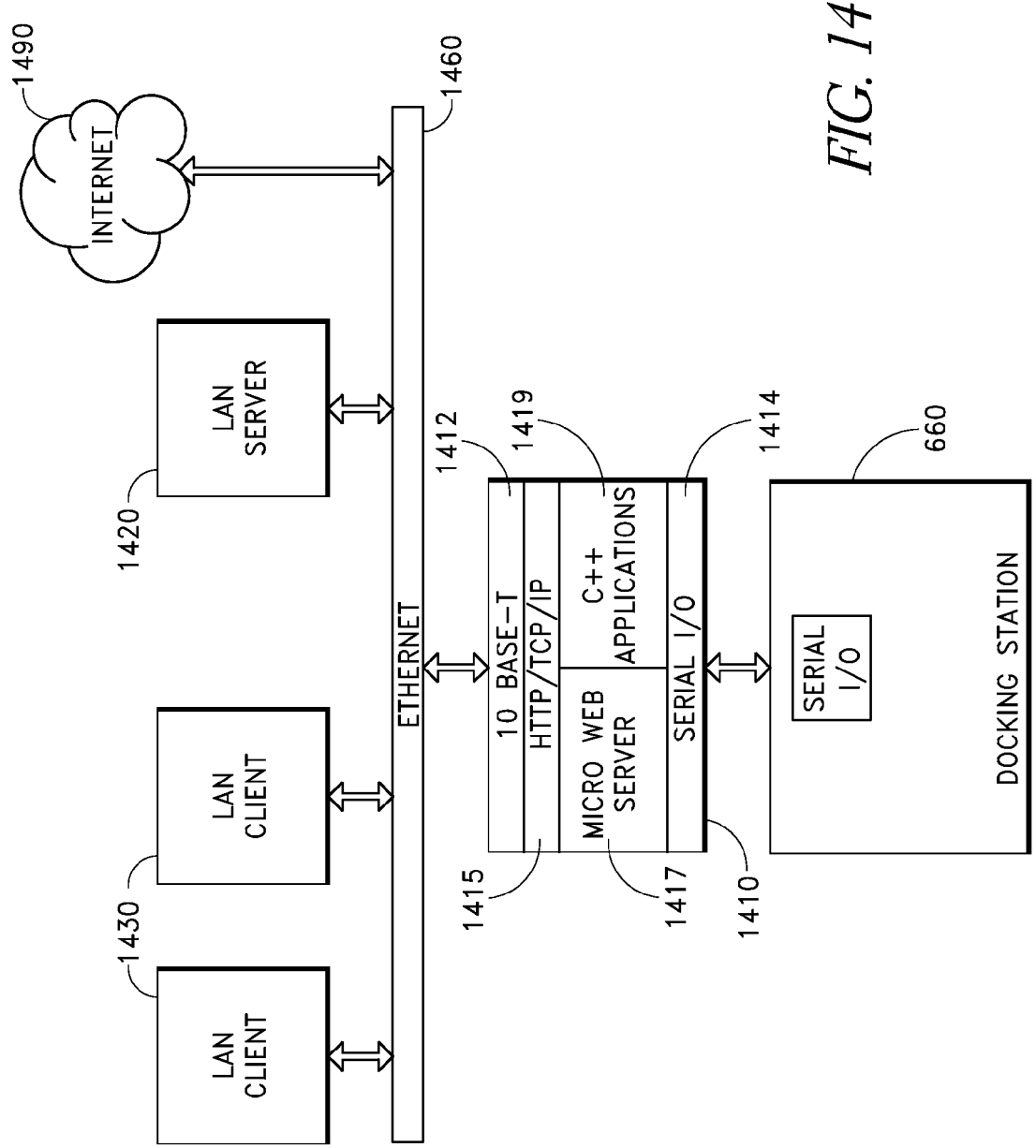
FIG. 14 is a block diagram of one embodiment of a local area network interface for a docking station.

FIG. 14 illustrates the docking station 660 incorporated within a local area network (LAN). The LAN shown is Ethernet-based 1460, using a central LAN server 1420 to interconnect various LAN clients 1430 and other system resources such as printers and storage (not shown). In this embodiment, an Ethernet controller module 1410 is incorporated with the docking station 660. The controller module 1410 can be incorporated within the docking station 660 housing or constructed as an external unit. In this manner, the UPO, according to the present invention, can communicate with other devices on the LAN or over the Internet 1490.

The Ethernet controller module 1410 can be embedded with web server firmware, such as the Hewlett-Packard (HP) BFOOT-10501. The module 1410 has both a 10 Base-T Ethernet interface for connection to the Ethernet 1460 and a serial interface, such as RS-232 or USB, for connection to the docking station 660. The module firmware incorporates HTTP and TCP/IP protocols for standard communications over the World Wide Web. The firmware also incorporates a micro web server that allows custom web pages to be served to remote clients over the Internet, for example. Custom C++ programming allows expanded capabilities such as data reduction, event detection and dynamic web page configuration.

As shown in FIG. 14, there are many applications for the docking station 660 to Ethernet interface. Multiple UPOs can be connected to a hospital's LAN, and a computer on the LAN could be utilized to upload pulse rate and saturation data from the various UPOs, displaying the results. Thus, this Ethernet interface could be used to implement a central pulse oximetry monitoring station within a hospital. Further, multiple UPOs from anywhere in the world can be monitored from a central location via the Internet. Each UPO is addressable as an individual web site and downloads web pages viewable on a standard browser, the web pages displaying oxygen saturation, pulse rate and related physiological measurements from the UPO. This feature allows a caregiver to monitor a patient regardless of where the patient or caregiver is located. For example a caregiver located at home in one city or at a particular hospital could download measurements from a patient located at home in a different city or at the same or a different hospital. Other applications include troubleshooting newly installed UPOs or uploading software patches or upgrades to UPOs via the Internet. In addition alarms could be forwarded to the URL of the clinician monitoring the patient.

The UPO may have other configurations besides the handheld unit described in connection with FIG. 5 or the portable 610 and docking station 660 combination described in connection with FIGS. 11-13. The UPO may be a module, with or without a display, that can be removably fastened to a patient via an arm strap, necklace or similar means. In a smaller embodiment, this UPO module may be integrated into a cable or connector used for attaching a sensor to a pulse oximeter. The UPO may also be a circuit card or module that can externally or internally plug into or mate with a standalone pulse oximeter or multiparameter patient monitoring system. Alternatively, the UPO may be configured as a simple standalone upgrade instrument.

Figure 15:
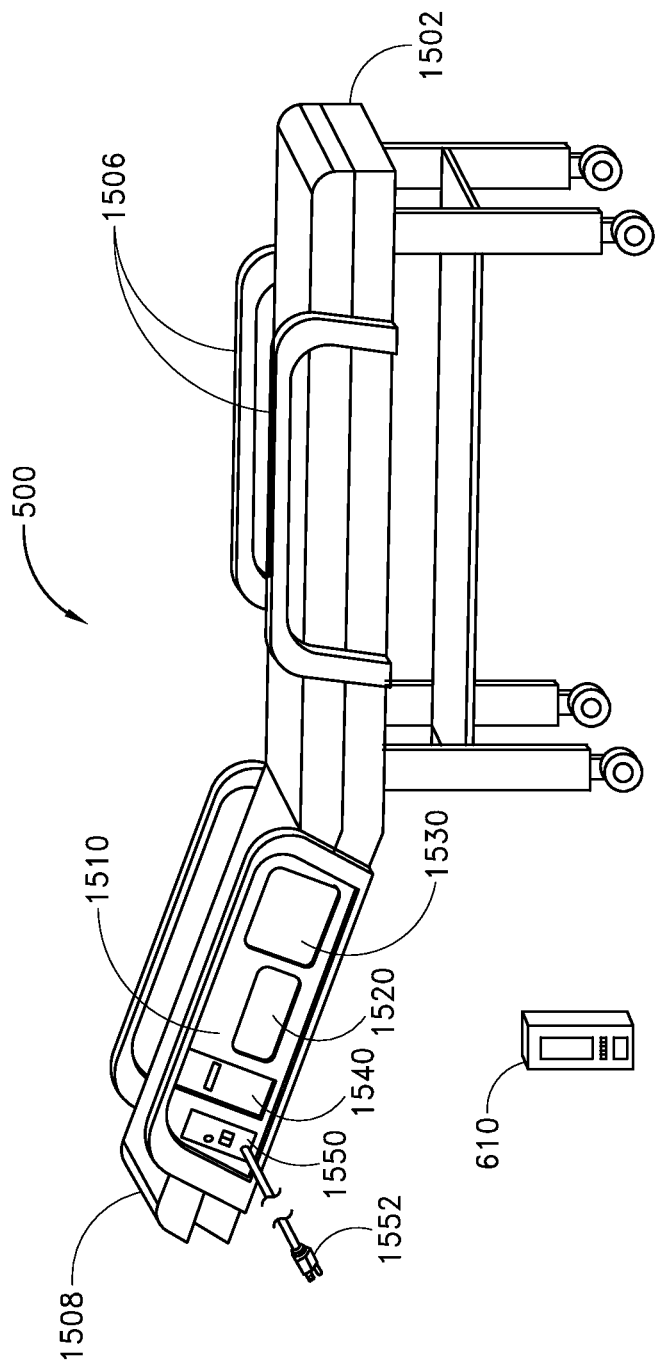
FIG. 15 is a perspective view of a patient care bed incorporating a docking station.

FIG. 15 illustrates a UPO configuration utilizing a patient care bed 1500. The bed 1500 includes a bed frame and mattress 1502, lower rails 1506 and upper rails 1508. One of the upper rails 1508 incorporates an instrument panel 1510 and the docking station 1540 is incorporated into the instrument panel 1510 according to the present invention. The instrument panel 1510 typically has keypad controls 1520, a display 1530, and a power supply 1550. The power supply 1550 has a power cord 1552 that plugs into an AC power source. The docking station 1540 includes a docking station compartment that accepts and electrically connects to the portable 610. In this manner, UPO can monitor a patient as a portable 610 during transport and then dock at the patient's destination as an integral part of the bedside instrument panel 1510.

Figure 16:
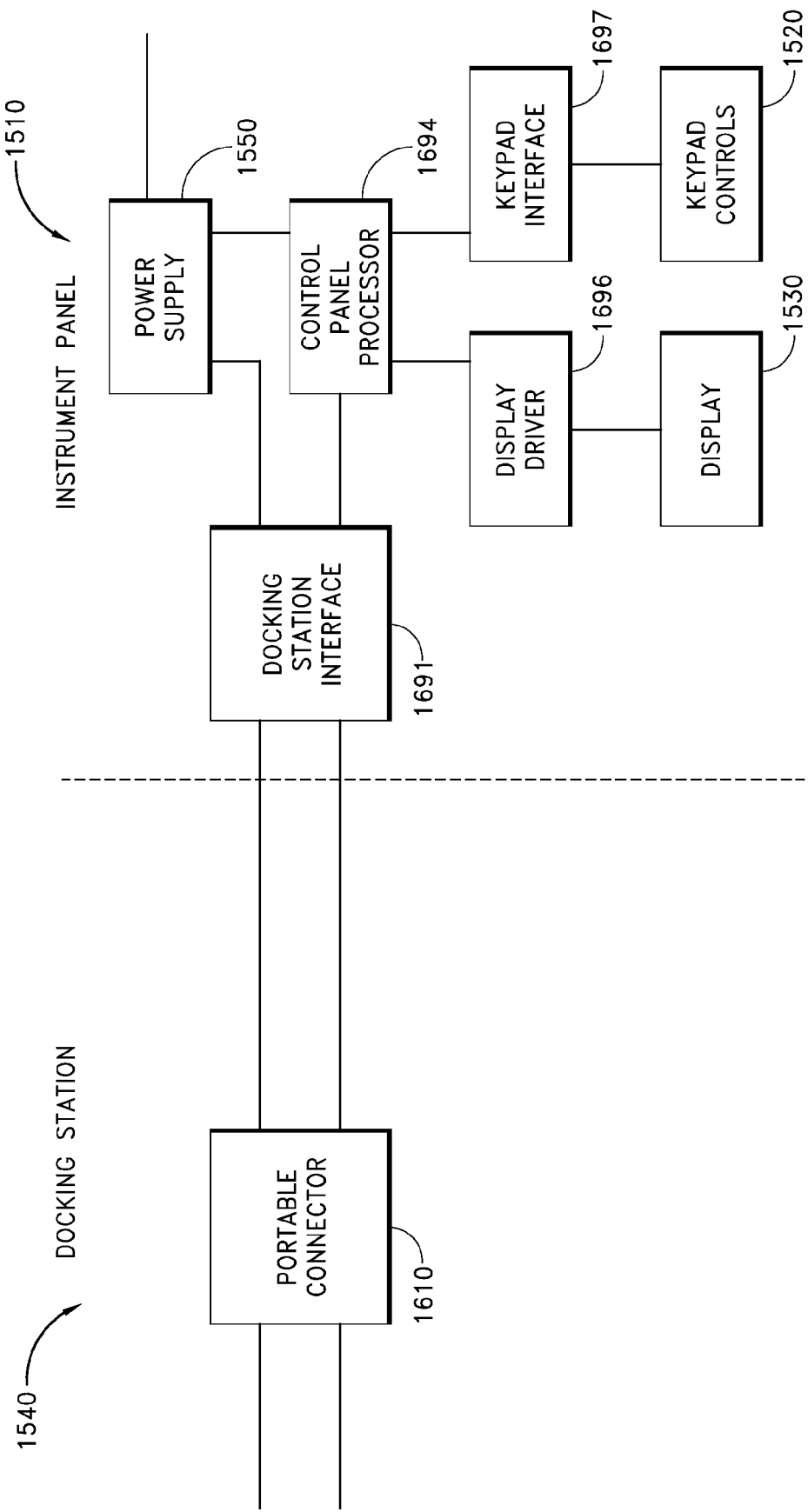
FIG. 16 is a block diagram of a docking station integrated into a patient care bed.

FIG. 16 is block diagram of the instrument panel 1510 and incorporated docking station 1540. The instrument panel 1510 has a processor 1694, which, in conjunction with a display driver 1696 and a keypad interface 1697, drives the display 1530 and receives commands from the keypad controls 1520. The processor 1694 also communicates with a docked portable 610 (FIG. 6) via the docking station interface 1691 and a portable connector 1610 within the docking station receptacle. In one embodiment, the docking station 1540 simply provides a communications path and a DC power path between the docked portable 610 (FIG. 6) and the instrument panel 1510 via the portable connector 1610 and the docking station interface 1690. In that embodiment, the portable management processor 720 (FIG. 7) is programmed with the communications protocol of the instrument panel processor 1694. In another embodiment, the docking station 1540 provides communications and upgrade capability in a manner similar to that shown in FIG. 9. In that embodiment, the bed-integrated UPO could also connect to and upgrade a MPMS pulse oximeter module 260 (FIG. 2) or other external pulse oximeter located near the patient bed 1500, in a manner as described with respect to FIG. 2, above.

Although a universal/upgrading apparatus and method have been mainly described in terms of a pulse oximetry measurement embodiment, the present invention is equally applicable to other physiological measurement parameters such as blood pressure, respiration rate, EEG, ECG and $EtCO_2$ (capnography) to name a few. In addition, a universal/ upgrading instrument having a single physiological measurement parameter or a multiple measurement parameter capability and configured as a handheld, standalone, portable, docking station, module, plug-in, circuit card, to name a few, is also within the scope of the present invention.

Figure 17A:
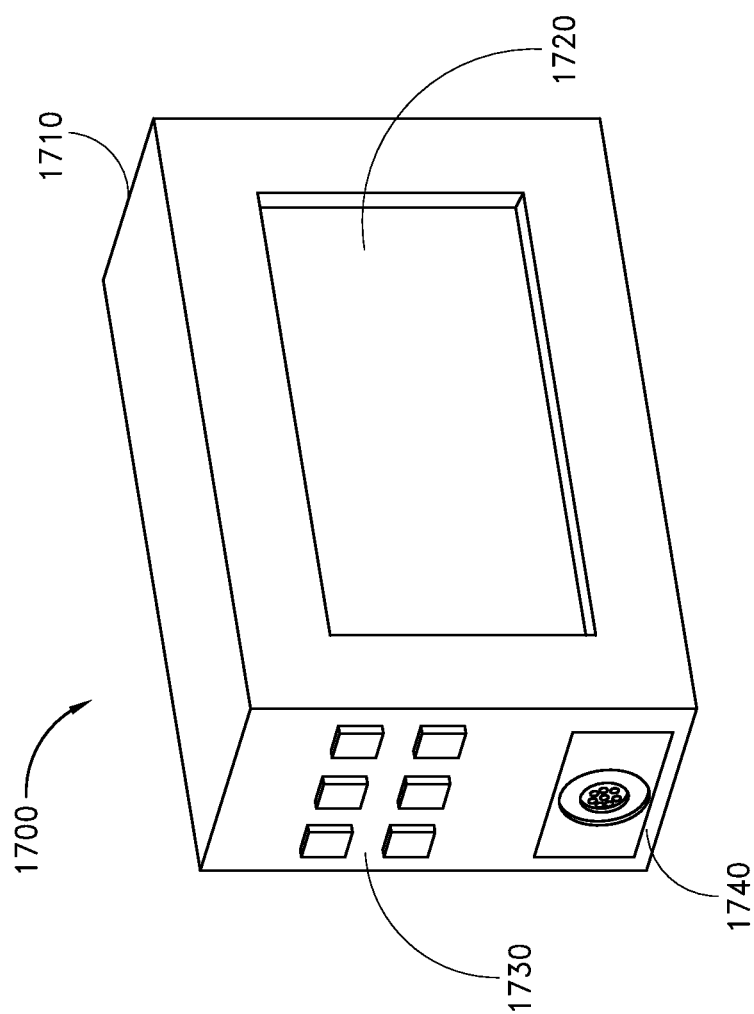
FIGS. 17A-B are front and back perspective views of a dual-mode pulse oximeter module according to the present invention.
Figure 17B:
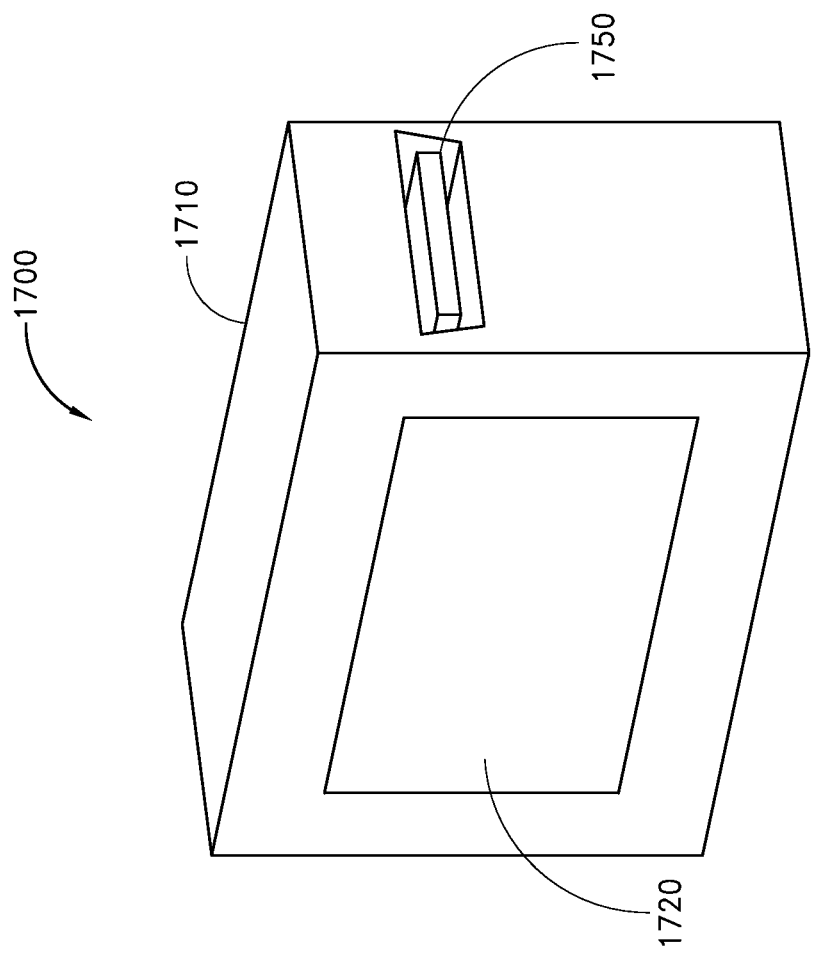

FIGS. 17A-B illustrate one embodiment of a dual-mode pulse oximeter module according to the present invention. As shown in FIG. 17A, a dual-mode pulse oximeter module 1700 is contained within a case 1710 having dimensions that conform to a multiparameter patient monitoring system (MPMS) slot 290 (FIG. 2). The dual-mode module 1700 has a display 1720, a keypad 1730, and a patient cable connector 1740. A module connector 1750 (FIG. 17B) mates and electrically connects with a corresponding backplane connector (not shown) within an MPMS slot 292 (FIG. 2).

In reference to FIGS. 17A-B, the dual-mode pulse oximeter module 1700 has a portable mode, separate from MPMS 250 (FIG. 2), and an integrated mode, plugged into an MPMS slot 292 (FIG. 2). In the portable mode, the pulse oximeter module 1700 functions as a handheld or standalone pulse oximeter, in a manner similar to that described with respect to FIG. 6, above. Specifically, the portable module 1700 is a battery-powered, pulse oximeter instrument. The portable module 1700 connects to a sensor through a patient cable attached to the patient cable connector 1740. The module 1700 provides the sensor with a drive signal that alternately activates the sensor's red and IR LEDs, as is well-known in the art. The pulse oximeter module 1700 also receives a corresponding photo-plethysmographic detector signal from the sensor, also well-known in the art. The portable module 1700 processes this sensor signal to derive oxygen saturation and pulse rate measurements. In the portable mode, this information is provided on the module display 1720, and a keypad 1730 provides a user interface for operational control of the portable module 1700.

Also in reference to FIGS. 17A-B, in the integrated mode, the pulse oximeter module 1700 is a plug-in module that functions in conjunction with the MPMS 250 (FIG. 2). When installed in a MPMS slot 290 (FIG. 2), the integrated module 1700 receives power from the MPMS 250 (FIG. 2), drives a sensor, receives a corresponding photo-plethysmographic sensor signal, and processes this sensor signal to derive oxygen saturation and pulse rate measurements, as described with respect to the portable mode, above. The integrated module 1700, however, communicates oxygen saturation, pulse rate and related measurements to the MPMS 250 (FIG. 2) via the module connector 1750. Typically, the integrated module display 1720 and keypad 1730 are disabled, and the MPMS monitor 280 (FIG. 2) displays the physiological measurements made by the integrated module 1700.

Figure 18:
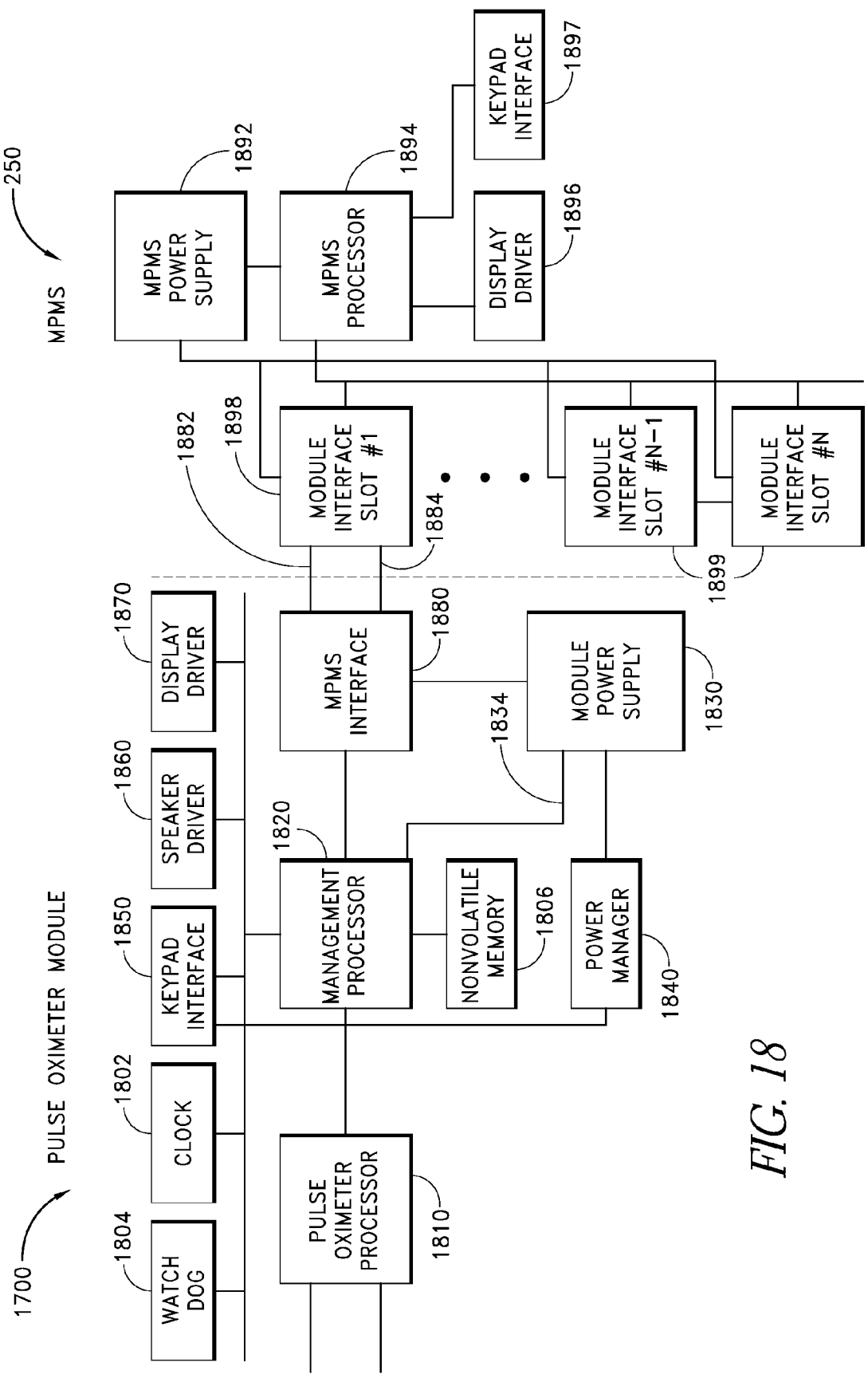
FIG. 18 is a block diagram of the dual-mode pulse oximeter module.

FIG. 18 is a block diagram of the dual-mode pulse oximeter module 1700. The pulse oximeter module 1700 includes a pulse oximeter processor 1810, management processor 1820, power supply 1830, power manager 1840, keypad interface 1850, speaker driver 1860, display driver 1870, clock 1802, watch dog timer 1804, and MPMS interface 1880. These components function in a manner similar to that described with respect to FIG. 7, above. Specifically, the pulse oximeter processor 1810 functions as an internal pulse oximeter, interfacing the pulse oximeter module 1700 to a sensor and deriving oxygen saturation, pulse rate, a plethysmograph and a pulse indicator.

As shown in FIG. 18, the management processor 1820 controls the various functions of the pulse oximeter module 1700, including data communications with the pulse oximeter processor 1810 and communications with the MPMS 250 via the MPMS interface 1880. The physical connection to the MPMS 250 is via the module connector 1750 (FIG. 17B) and a corresponding MPMS backplane connector. The electrical connection is via a module interface 1898. The management processor 1820 utilizes a real-time clock 1802 to keep the current date and time, which includes time and date information that is stored in nonvolatile memory 1806 along with oxygen saturation related parameters to create trend data. The management processor 1820 also controls a user interface by transferring data to a display driver 1870 and from a keypad interface 1850. The management processor 1820 generates various alarm signals, which control a speaker driver 1860. The management processor 1820 also monitors system status, which includes battery status, indicating battery levels, and plug-in status, indicating whether the pulse oximeter module 1700 is connected to the MPMS 250. Another task of the management processor 1820 includes maintenance of a watchdog function. A watchdog 1804 monitors processor status on the watchdog data input and asserts a management processor reset if a fault is detected, along with audible and visual alarms.

Also shown in FIG. 18, the pulse oximeter module 1700 gets its power from batteries in the power supply 1830 or from power supplied on line 1884 from the MPMS 250 via the MPMS interface 1880. A power manager 1840 monitors the keypad on/off switch via the keypad interface 1850 and turns-on module power 1830 accordingly. The power manager 1840 turns off module power 1830 on command by the management processor 1820. DC/DC converters within the power supply 1830 generate the required voltages for module operation. A battery charger within the module power supply 1830 provides charging current to recharge the internal batteries. A non-volatile memory 1806 is connected to the management processor 1820 and used to store boot data, alarm limits trend data and program data.

Figure 19:
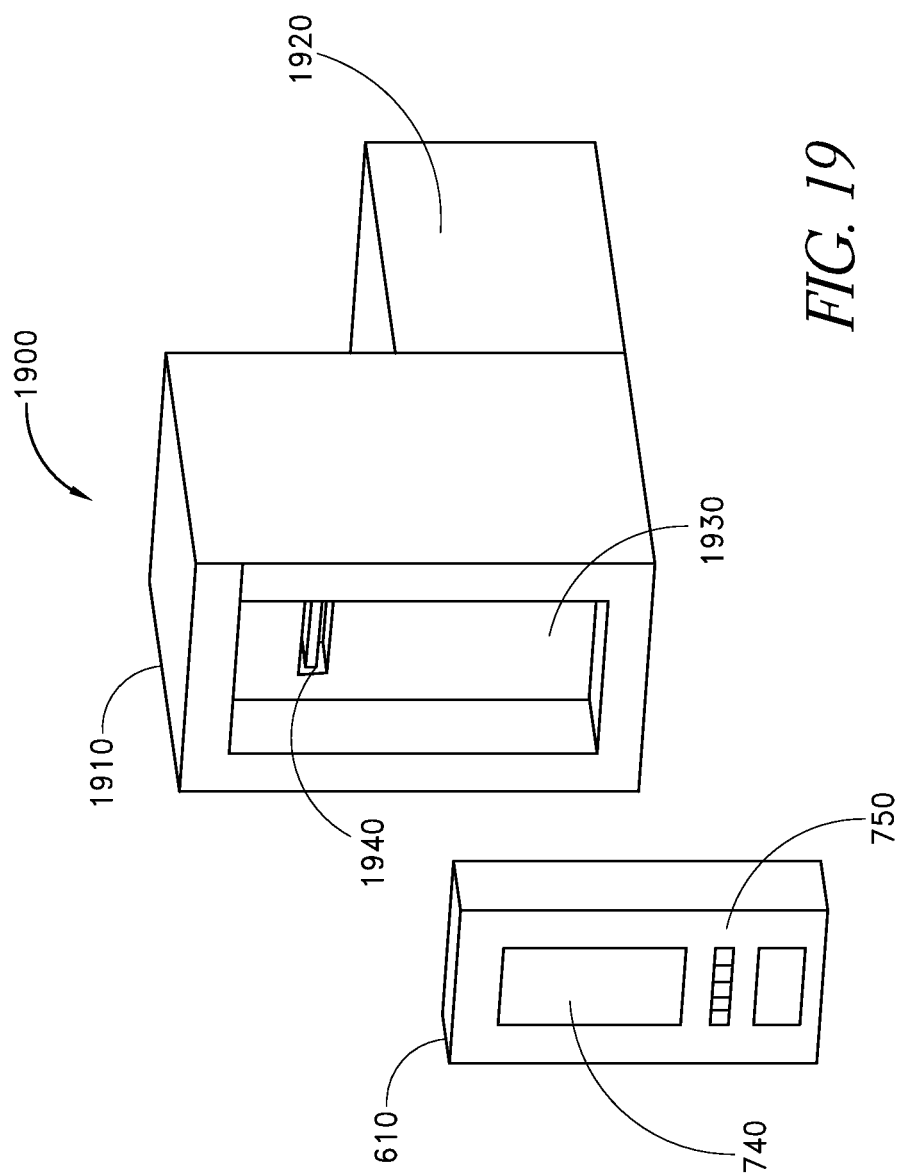
FIG. 19 is a perspective view of a docking station module according to the present invention.

FIG. 19 illustrates another embodiment of a dual-mode pulse oximeter according to the present invention. A docking station module 1900 has a docking portion 1910 and a plug-in portion 1920. The docking portion 1910 has a docking compartment 1930 and a portable socket 1940. The docking compartment 1930 is configured to accept and retain a portable pulse oximeter 610, such as described with respect to FIGS. 6 and 11A-B, above. In particular, the portable 610 has a socket 763 (FIG. 11B) that mates with a corresponding plug 1940, providing an electrical connection between the portable pulse oximeter 610 and the docking station module 1900. The plug-in portion 1920 has dimensions that conform to an MPMS slot 290 (FIG. 2). A module connector similar to that of the pulse oximeter module connector 1750 (FIG. 17B) mates and electrically connects with a corresponding backplane connector (not shown) within an MPMS slot 290 (FIG. 2).

In reference to FIG. 19, the docking station module 1900 allows the portable 610 to function as a dual-mode pulse oximeter. That is, the portable 610 has a portable mode separate from the MPMS 250 (FIG. 2) and an integrated mode connected to an MPMS slot 290 (FIG. 2) via the docking station module 1900. In this manner, the portable 610 functions much as the dual-mode module 1700 (FIGS. 17A-B) described with respect to FIGS. 17A-B, above. In the portable mode, the portable 610 functions as a handheld or standalone pulse oximeter as described with respect to FIG. 6, above. In the integrated mode, the portable 610 is docked to the docking station module 1900 and functions in conjunction with the MPMS 250 (FIG. 2). When installed in an MPMS slot 290 (FIG. 2), the portable receives power from a MPMS 250 (FIG. 2), drives a sensor, receives a corresponding photo-plethysmographic sensor signal, and processes this sensor signal to derive oxygen saturation and pulse rate measurements, as described with respect to FIG. 6, above. The integrated portable 610, however, communicates oxygen saturation, pulse rate and related measurements to the MPMS 250 (FIG. 2) via the docking station module 1900, as described below. Typically, the portable display 740 and keys 750 are disabled, and the MPMS monitor 280 (FIG. 2) controls and displays the physiological measurements made by the integrated portable 610.

Also in reference to FIG. 19, in an alternative embodiment, the docking compartment 1930 is configured to accept and retain a pulse oximeter module 1700 (FIGS. 17A-B). In that embodiment, the docking compartment 1930 has a docking connector (not shown) that mates with the module connector 1750 (FIG. 17B), providing an electrical connection between the pulse oximeter module 1700 (FIGS. 17A-B) and the docking station module 1900.

Figure 20:
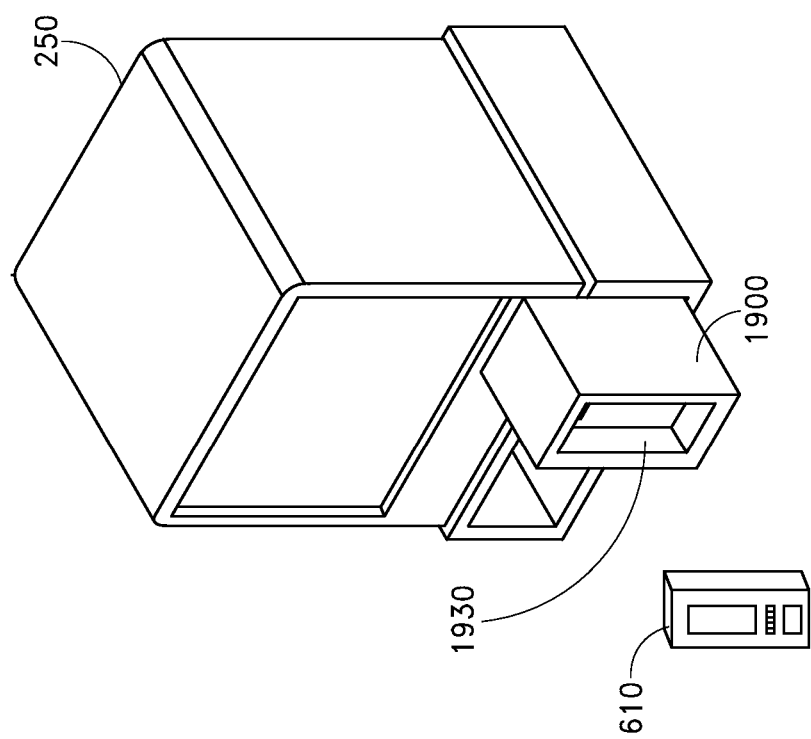
FIG. 20 is a perspective view of the docking station module of FIG. 19 attached to a multiparameter patient monitoring system (MPMS)

FIG. 20 illustrates the docking station module 1900 attached to the MPMS 250. The plug-in portion 1920 (FIG. 19) plugs into at least one of the MPMS slots 290 (FIG. 2) and electrically connects to the MPMS backplane as described with respect to FIG. 19, above. In the portable mode (shown), the portable pulse oximeter 610 functions in a manner similar to the portable module 1700 (FIGS. 17A-B), i.e. as handheld or standalone pulse oximeter. In the integrated mode, the portable 610 is installed into the docking compartment 1930, providing an electrical connection and communications interface between the MPMS 250 and the portable pulse oximeter 610. In the integrated mode, the combination of the portable pulse oximeter 610 and the docking station module 1900 functions in a manner similar to the integrated module 1700 (FIGS. 17A-B).

Figure 21:
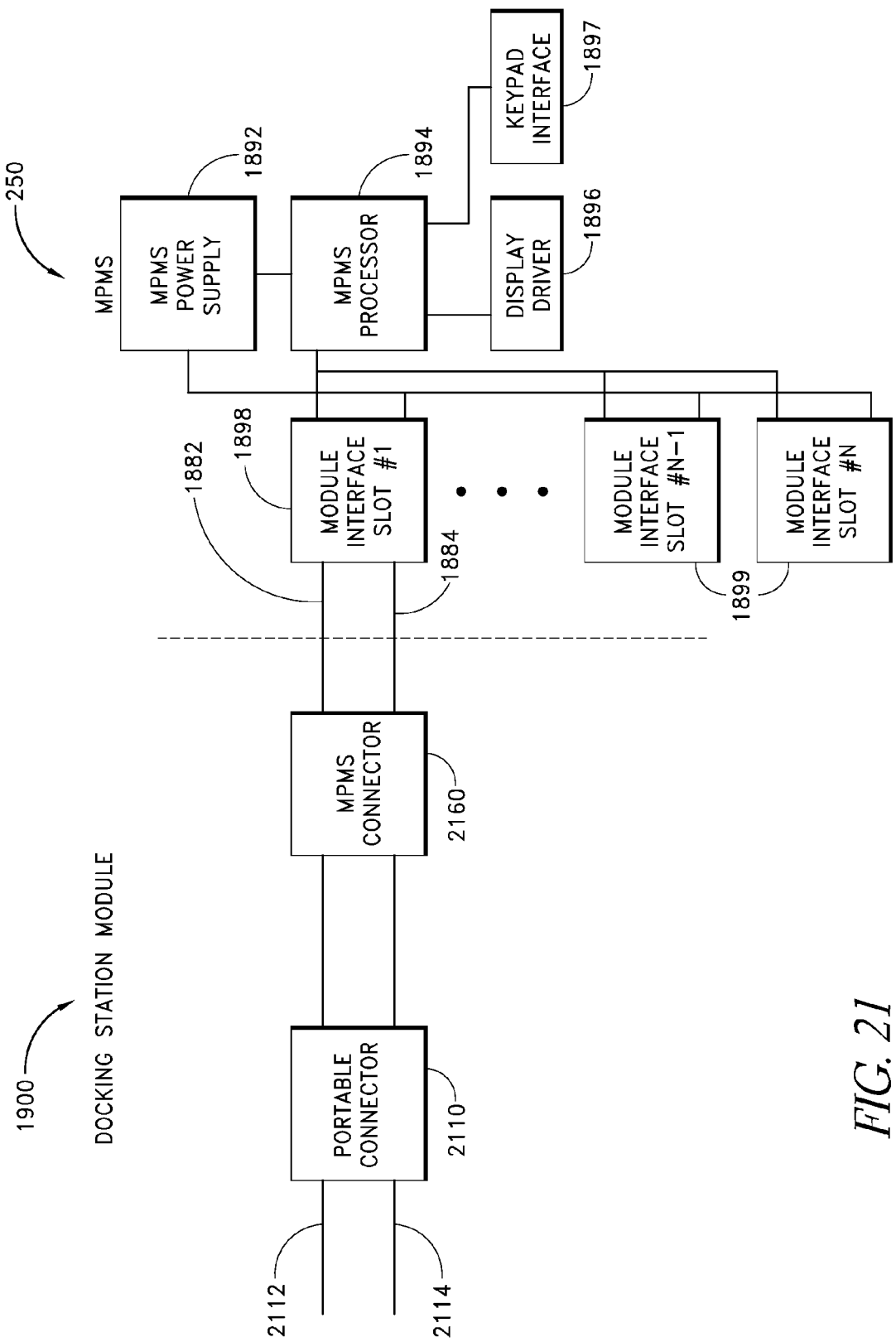
FIG. 21 is a block diagram of a pass-through docking station module.

FIG. 21 is a block diagram of a pass-through embodiment of a docking station module 1900, which includes a portable connector 2110, an MPMS connector 2160 and a direct electrical path between the two connectors 2110, 2160. In this embodiment, the docking station module 1900 simply provides a physical interface between the portable 610 (FIG. 20) and the MPMS 250. A MPMS communications path 1882 is directly routed to the portable communications path 2112. MPMS power 1884 is also directly routed to the portable input power line 2114. The docking station module 1900, with various configurations of the plug-in portion 1920 (FIG. 19) and associated module connector can be adapted to the slots 290 (FIG. 2) of various MPMS manufacturers. In this manner, the docking station module 1900 can function as a universal interface between the portable pulse oximeter 610 or, alternatively, the pulse oximeter module 1700 and various multiparameter patient monitoring systems.

Figure 22:
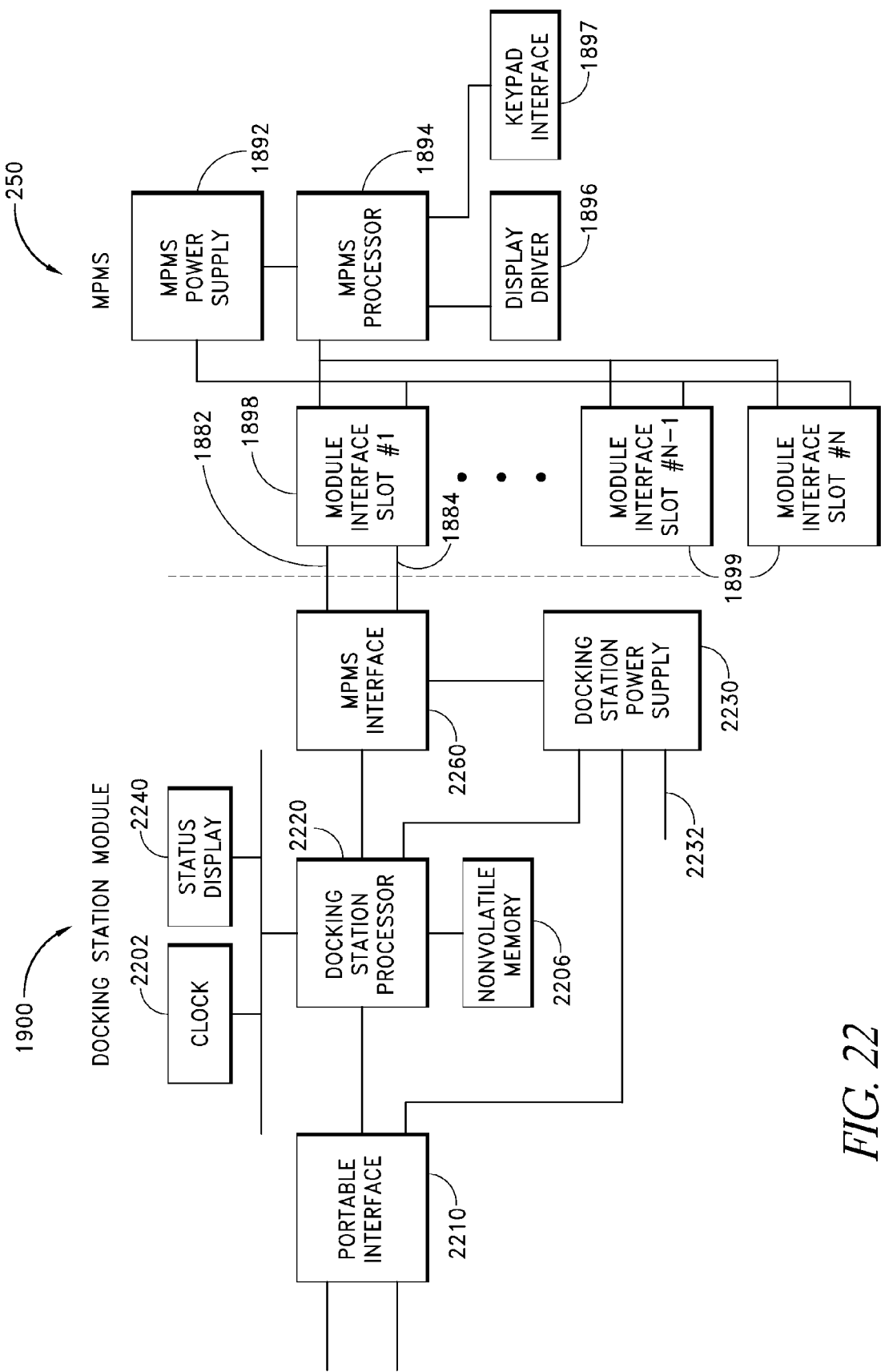
FIG. 22 is a block diagram of a docking station module providing an MPMS interface.

FIG. 22 is a block diagram of another embodiment of a docking station module 1900a, which includes a portable interface 2210, docking station processor 2220, power supply 2230 and monitor interface 2260. These components function in a manner similar to that described with respect to FIG. 9, above. Specifically, the docking station processor 2220 orchestrates the activity of the docking station module 1900. The processor 2220 provides synchronous serial data for communications with the portable 610 (FIG. 6) and sends watchdog messages to the portable processor 720 (FIG. 7) as part of the synchronous serial data to ensure the correct operation of the docking station processor 2220. The docking station processor 2220 accesses non-volatile, re-programmable memory 2206 over a high-speed bus to obtain program data for the processor 2220. In one embodiment, the status display 2240 is a set of LEDs on the front of the docking station module 1900 used to indicate various conditions including portable docked, portable battery charging and alarm. The portable interface 2210 interconnects with the docking station interface 760 (FIG. 7) of the portable 610 (FIG. 6). External power 1884 is provided to the docking station module 1900a from the MPMS 250. The docking station power supply 2230 charges the battery in the portable power supply 730 (FIG. 7). When the portable 610 (FIG. 6) is either removed or turned off, the docking station power 2232 is removed and the docking station 1900 is turned off, except for the battery charger portion of the power supply 2230. The docking station power 2232 and, hence, the docking station 1900 turns on whenever a docked portable 610 (FIG. 6) is turned on.

Although the dual-mode physiological measuring apparatus and method of the present invention is described in detail with respect to pulse oximetry measurements, one of ordinary skill in the art will recognize that a dual-mode MPMS plug-in module or a portable apparatus that docks to a MPMS plug-in docking station module could incorporate physiological measurement capabilities other than or in addition to pulse oximetry, such as blood pressure, respiration rate, EEG, ECG and $EtCO_2$ (capnography) to name a few.

The dual-mode pulse oximeter has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A physiological monitoring system including a portable physiological monitor and a docking station coupled to a patient bed, the physiological monitoring system comprising:
    a portable physiological monitor including a first local display and a processor, the monitor configured to operate in a portable mode, said portable mode providing portable monitoring as a standalone patient monitor of one or more physiological parameters of a patient through communication with one or more sensors, and configured to operate in a docked mode, said docked mode providing monitoring of one or more physiological parameters of a patient;
    a docking station including an integrated second local display, the docking station coupled to a patient bed, said docking station configured to mate with the portable physiological monitor when the monitor is operating in at least the docked mode, wherein the portable physiological measurement device is in communication with the docking station, and further wherein the docking station is in communication with the second local display; and
    a management processor that generates an output usable by an alternative patient monitoring system in communication with the docking station to cause to be displayed at least one of the monitored one or more physiological parameters of the patient in an amount consistent with those displayed on the portable physiological monitor when the portable physiological monitor is operating in at least the docked mode.

2. The physiological monitoring system of claim 1, wherein the one or more physiological parameters comprises blood oxygen saturation.

3. The physiological monitoring system of claim 2, wherein the portable physiological monitor is configured to substantially accurately measure blood oxygen saturation in the presence of motion induced noise.

4. The physiological monitoring system of claim 1, wherein the docking station is communicatively coupled to the alternative patient monitoring system so as to be configured to send a sensor signal to the alternative patient monitoring system.

5. The physiological monitoring system of claim 4, wherein the alternative patient monitoring system communicates with a display device.

6. The physiological monitoring system of claim 1, wherein the one or more physiological parameters comprises one or more of blood oxygen content, respiratory gas, blood pressure, ECG, and pulse rate.

7. A multi-monitor system for monitoring physiological parameters of a patient, the system comprising:
a portable monitor including a portable display and a portable processor, said portable monitor configured to operate in a portable mode and a docked mode, said portable monitor also configured to communicate with a noninvasive sensor, said portable processor configured to process signals from said noninvasive sensor to determine display values of physiological parameters of the patient, wherein when operating in said portable mode, said portable monitor operates as a standalone monitor to communicate at least some of said display values to said portable display for caregiver review; and
a multi-parameter monitor associated with a processor other than said portable processor, a display other than said portable display, and a docking receptacle, said multi-parameter processor configured to process signals other than said signals from said noninvasive sensor associated with said portable monitor to determine display values of physiological parameters of the patient and to communicate at least some of said determined display values to said display for caregiver review, said docking receptacle configured to mechanically accept and physically position said portable monitor with respect to said multi-parameter monitor, and wherein when said portable monitor operates in said docked mode, said portable monitor communicates with said multi-parameter processor to communicate at least some of said display values to said multi-parameter display for caregiver review.

8. The multiple-monitor system of claim 7, wherein said physiological parameters include at least one of oxygen saturation, pulse rate, respiration rate, blood pressure, EEG, and ECG.

9. The multiple-monitor system of claim 7, wherein said communications of said some display values from said portable monitor to said multi-parameter processor includes a synthesized waveform.

10. The multiple-monitor system of claim 9, wherein said synthesized waveform is calculated with reference to a waveform look-up table.

11. The multiple-monitor system of claim 9, wherein said synthesized waveform is stored in memory and is configured to be manually synchronized at a later time during said communications.

12. The multi-monitor system of claim 7, wherein said docking receptacle includes a module slot portion.

13. The multiple-monitor system of claim 7, wherein when said portable monitor operates in said docked mode, said portable display does not display at least one of said display values.

14. A patient monitor comprising:
a first display;
a first processor configured to receive a first signal indicative of at least one physiological parameter of a monitored patient from a first non-invasive sensor and further configured to process said first signal to determine a first measurement, and to communicate said first measurement to said first display for caregiver review;
a second display;
a second processor configured to operate in a portable mode and a docked mode, and configured to receive a second signal from a second noninvasive sensor, said second processor configured to process said second signal to determine at least a second measurement, and to communicate said second measurement to said second display for caregiver review;
a housing arranging said second display and said second processor as a portable standalone monitoring device away from said first display and said first processor; and
a docking station configured to physically position said housing with respect to said first display and configured to provide communication between said first and second processors in order for said first processor to receive an indication of said second measurement and to communicate said second measurement to said first display when said second processor is operating in said docked mode.

15. The patient monitor of claim 14, wherein said second measurement comprises one of oxygen saturation, pulse rate, respiration rate, blood pressure, EEG, and ECG.

16. The patient monitor of claim 14, wherein said first measurement comprises a plurality of first measurements.

17. The patient monitor of claim 14, wherein said second measurement comprises a plurality of second measurements.

18. The patient monitor of claim 14, wherein said first measurement is different from said second measurement.

19. The patient monitor of claim 14, wherein said first measurement is for the same physiological parameter as said second measurement.

20. The patient monitor of claim 14, wherein said first processor receives at least a portion of said second measurement by synthesized waveform.

21. The patient monitor of claim 14, wherein said docking station configured to physically position said housing includes a module slot portion.

22. A method of providing measurements for caregiver review, the method comprising:
receiving at a standalone handheld portable patient monitor first signals indicative of physiological parameters of a monitored patient from a first physiological sensor;
processing said first signals to determine one or more first measurements using a first processor of said standalone handheld portable patient monitor;
communicating said one or more first measurements to a first display for caregiver review;
docking said standalone portable patient monitor including said first processor and said first display using a docking station, said docking station including a second display, and a second processor;
receiving at said docking station second signals indicative of second physiological parameters of a monitored patient from a second physiological sensor associated with said docking station;
processing said second signals using said second processor to determine one or more second measurements;
communicating said second measurements to said second display for caregiver review;
receiving at said docking station at least one of said one or more first measurements; and
communicating an indication of said first measurements to said second display for caregiver review.

23. The method of claim 22, wherein at least some of said second measurements are different from said first measurements.

24. The method of claim 22, wherein the step of receiving at said docking station at least one of said one or more first measurements further comprises receiving a synthesized waveform.

25. The method of claim 24, wherein the step of receiving a synthesized waveform at said docking station further comprises receiving a synthesized waveform generated by manual synchronization at said standalone handheld portable patient monitor.

26. The method of claim 22, wherein the step of docking said standalone portable patient monitor further comprises docking said standalone handheld portable patient monitor in a module slot portion at said docking station.

* * * * *

UNITED STATES PATENT AND TRADEMARK OFFICE
CERTIFICATE OF CORRECTION

PATENT NO. : 8,532,727 B2  
APPLICATION NO. : 11/894722  
DATED : September 10, 2013  
INVENTOR(S) : Ali et al.

Page 1 of 2

It is certified that error appears in the above-identified patent and that said Letters Patent is hereby corrected as shown below:

On the Title Page

Page 1 (item 75, Inventors) at line 1, Change "Irvine, CA" for Julian Goldman to --Newton, MA--.

In column 1 (page 3 item 56) at line 20, Under U.S. Patent Documents, change "Diab" to --Diab et al.--.

In column 2 (page 4 item 56) at line 60, Under Other Publications, change "Eno. Cornput.," to --Eng. Comput.,--.

In column 1 (page 5 item 56) at line 40, Under Other Publications, change "Office Office" to --Office--.

In column 1 (page 5 item 56) at line 42, Under Other Publications, change "Office Office" to --Office--.

In column 1 (page 5 item 56) at line 44, Under Other Publications, change "Office Office" to --Office--.

In column 1 (page 5 item 56) at line 46, Under Other Publications, change "Office Office" to --Office--.

In column 1 (page 5 item 56) at line 48, Under Other Publications, change "Office Office" to --Office--.

In column 1 (page 5 item 56) at line 50, Under Other Publications, change "Office Office" to --Office--.

In column 1 (page 5 item 56) at line 52, Under Other Publications, change "Office Office" to --Office--.

In column 1 (page 5 item 56) at line 54, Under Other Publications, change "Office Office" to --Office--.

Signed and Sealed this  
Eighth Day of July, 2014

Michelle K. Lee  
*Deputy Director of the United States Patent and Trademark Office*

In column 1 (page 5 item 56) at line 56, Under Other Publications, change "Office Office" to --Office--.

In column 2 (page 5 item 56) at line 57, Under Other Publications, change "Corporationv." to --Corporation v.--.

In the Drawings

Sheet 3 of 25 (FIG. 3) at line 3 (approx.), Change "160" to --260--.

Sheet 6 of 25 (FIG. 6, Ref. Numeral 692) at line 1, Change "SVNC" to --SYNC--.

Sheet 7 of 25 (FIG. 7, Ref. Numeral 724) at line 1, Change "ASVNC." to --ASYNC.--.

Sheet 7 of 25 (FIG. 7, Ref. Numeral 762) at line 1, Change "SVNC." to --SYNC.--.

Sheet 7 of 25 (FIG. 7, Ref. Numeral 736) at line 1, Change "BATERRY" to --BATTERY--.

Sheet 9 of 25 (FIG. 9, Ref. Numeral 912) at line 1, Change "ASVNC" to --ASYNC--.

Sheet 9 of 25 (FIG. 9, Ref. Numeral 942) at line 1, Change "SVNC" to --SYNC--.

Sheet 9 of 25 (FIG. 9, Ref. Numeral 692) at line 1, Change "SVNC" to --SYNC--.

Sheet 9 of 25 (FIG. 9, Ref. Numeral 971) at line 1, Change "SVNC." to --SYNC.--.

In the Specification

In column 9 at line 50, Change "bidirectional" to --bi-directional--.

In column 15 at line 62, Change "the:pole" to --the pole--.

In column 16 at line 13 (approx.), Change "1B)," to --11B),--.